US010463436B2

(12) United States Patent
Jackson et al.

(10) Patent No.: US 10,463,436 B2
(45) Date of Patent: Nov. 5, 2019

(54) DRIVE MECHANISMS FOR ROBOT ARMS

(71) Applicant: CMR SURGICAL LIMITED, Cambridge (GB)

(72) Inventors: Thomas Bates Jackson, Cambridge (GB); Luke David Ronald Hares, Cambridge (GB); Keith Marshall, Cambridge (GB); Steven James Randle, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 15/217,077

(22) Filed: Jul. 22, 2016

(65) Prior Publication Data
US 2017/0021507 A1 Jan. 26, 2017

(30) Foreign Application Priority Data

Jul. 22, 2015 (GB) .................................. 1512959.6

(51) Int. Cl.
*B25J 17/00* (2006.01)
*A61B 34/30* (2016.01)
(Continued)

(52) U.S. Cl.
CPC .............. *A61B 34/30* (2016.02); *B25J 9/102* (2013.01); *B25J 17/0258* (2013.01);
(Continued)

(58) Field of Classification Search
CPC ... A61B 34/30; B25J 17/0258; B25J 17/0275; B25J 18/04; B25J 9/102; F16H 19/001
See application file for complete search history.

(56) References Cited

U.S. PATENT DOCUMENTS 4,435,120 A 3/1984 Ikeda et al.
4,760,753 A 8/1988 Vetter et al.
(Continued)

FOREIGN PATENT DOCUMENTS

CN 104742152 A 7/2015
DE 10145234 A1 4/2003
(Continued)

OTHER PUBLICATIONS

International Search Report from corresponding PCT/GB2016/052264 dated Oct. 13, 2016.
(Continued)

*Primary Examiner* — Zakaria Elahmadi
(74) *Attorney, Agent, or Firm* — Lando & Anastasi, LLP

(57) ABSTRACT

A robot arm comprising a joint mechanism for articulating one limb of the arm relative to another limb of the arm about two non-parallel rotation axes, the mechanism comprising: an intermediate carrier attached to a first one of the limbs by a first revolute joint having a first rotation axis and to a second one of the limbs by a second revolute joint having a second rotation axis; a first drive gear disposed about the first rotation axis, the first drive gear being fast with the carrier; a second drive gear disposed about the second rotation axis, the second drive gear being fast with the second one of the limbs; a first drive shaft for driving the first drive gear to rotate about the first rotation axis, the first drive shaft extending along the first one of the limbs and having a first shaft gear thereon, the first shaft gear being arranged to engage the first drive gear; a second drive shaft for driving the second drive gear to rotate about the second rotation axis, the second drive shaft extending along the first one of the limbs and having a second shaft gear thereon, the second shaft gear being arranged to engage the second drive gear; the second drive shaft comprising a prismatic joint whereby
(Continued)

the length of the shaft can vary in response to motion of the carrier about the first axis.

13 Claims, 11 Drawing Sheets

(51) Int. Cl.
    *B25J 9/10*           (2006.01)
    *B25J 17/02*         (2006.01)
    *F16H 19/00*        (2006.01)
    *B25J 18/04*         (2006.01)
    *A61B 17/00*         (2006.01)

(52) U.S. Cl.
    CPC ........... *B25J 17/0275* (2013.01); *B25J 18/04* (2013.01); *F16H 19/001* (2013.01); *A61B 2017/0069* (2013.01); *A61B 2034/305* (2016.02); *Y10S 901/25* (2013.01); *Y10S 901/26* (2013.01)

(56) References Cited

U.S. PATENT DOCUMENTS

| | | | | |
|---|---|---|---|---|
| 4,761,114 | A * | 8/1988 | Barland | B25J 17/0283 414/735 |
| 4,776,232 | A | 10/1988 | Beyer | |
| 5,101,681 | A * | 4/1992 | Shpigel | B25J 17/0258 403/57 |
| 6,602,042 | B2 * | 8/2003 | Roy | B23Q 1/5462 414/735 |
| 6,871,563 | B2 * | 3/2005 | Choset | B25J 9/102 74/490.01 |
| 8,380,351 | B2 * | 2/2013 | Okuda | B25J 9/102 700/255 |
| 8,414,043 | B2 | 4/2013 | Albin et al. | |
| 8,616,088 | B2 * | 12/2013 | Teng | B25J 9/102 74/490.05 |
| 8,621,955 | B2 * | 1/2014 | Long | B25J 17/0258 74/490.1 |
| 8,663,060 | B2 * | 3/2014 | Cline | F16H 37/06 475/243 |
| 9,010,214 | B2 * | 4/2015 | Markvicka | A61B 34/30 606/130 |
| 2004/0250644 | A1 | 12/2004 | Gosselin et al. | |
| 2005/0275367 | A1 * | 12/2005 | Buehler | B25J 9/102 318/568.12 |
| 2012/0137816 | A1 * | 6/2012 | Carricato | B25J 17/0266 74/490.05 |
| 2013/0131695 | A1 * | 5/2013 | Scarfogliero | A61B 19/2203 606/130 |
| 2013/0345717 | A1 | 12/2013 | Markvicka et al. | |
| 2014/0001231 | A1 | 1/2014 | Shelton, IV et al. | |
| 2014/0005687 | A1 | 1/2014 | Prisco et al. | |
| 2015/0265355 | A1 | 9/2015 | Prestel et al. | |
| 2016/0008989 | A1 | 1/2016 | Bakir et al. | |
| 2016/0101518 | A1 | 4/2016 | Saito et al. | |
| 2016/0114479 | A1 | 4/2016 | Rosheim | |
| 2016/0135898 | A1 | 5/2016 | Frederick et al. | |
| 2016/0175062 | A1 * | 6/2016 | Limon | A61B 34/30 134/32 |
| 2016/0207206 | A1 | 7/2016 | Sato et al. | |
| 2016/0270780 | A1 | 9/2016 | Hall et al. | |
| 2017/0014197 | A1 | 1/2017 | McCrea et al. | |
| 2017/0049519 | A1 | 2/2017 | Grover et al. | |
| 2017/0265951 | A1 | 9/2017 | Grover et al. | |
| 2017/0304015 | A1 | 10/2017 | Tavallaei et al. | |

FOREIGN PATENT DOCUMENTS

| | | | | |
|---|---|---|---|---|
| DE | 102011108265 | A1 | 1/2013 | |
| EP | 0128544 | A1 * | 12/1984 | .......... B25J 17/0258 |
| EP | 0279591 | A1 | 8/1988 | |
| FR | 2504051 | A1 | 10/1982 | |
| FR | 2832345 | A1 | 5/2003 | |
| GB | 1565730 | A | 4/1980 | |
| JP | S6090693 | A | 5/1985 | |
| SU | 1151453 | A1 | 4/1985 | |
| WO | 2015088655 | A1 | 6/2015 | |
| WO | WO 2015088655 | A1 * | 6/2015 | .............. B25J 9/102 |
| WO | 2015132549 | A1 | 9/2015 | |

OTHER PUBLICATIONS

United Kingdom Search Report from corresponding United Kingdom Application No. GB1512959.6 dated Dec. 24, 2015.
United Kingdom Search Report from corresponding United Kingdom Application No. GB1612781.3 dated Jan. 3, 2017.
International Search Report from corresponding PCT/GB2016/052262 dated Dec. 5, 2016.
List of References Cited in U.S. Appl. No. 15/217,082.
Notification of Transmittal of the International Search Report and the Written Opinion of the International Searching Authority from corresponding PCT/GB2016/052262 dated Dec. 5, 2016.
United Kingdom Search Report from corresponding United Kingdom Application No. GB1512960.4 dated Dec. 24, 2015.

* cited by examiner

DRIVE MECHANISMS FOR ROBOT ARMS

CROSS-REFERENCE TO RELATED APPLICATION

This application claims the benefit under 35 U.S.C. § 119 of United Kingdom Patent Application No. 1512959.6 filed on Jul. 22, 2015 which is hereby incorporated herein by reference in its entirety for all purposes.

This application also relates to U.S. patent application Ser. No. 15/217,035 entitled DRIVE MECHANISMS FOR ROBOT ARMS, by Thomas Bates Jackson, Luke David Ronald Hares, Keith Marshall and Steven James Randle, filed on even date herewith, and U.S. patent application Ser. No. 15/217,061 entitled DRIVE MECHANISMS FOR ROBOT ARMS, by Thomas Bates Jackson, Luke David Ronald Hares, Keith Marshall and Steven James Randle, filed on even date herewith. All of these related applications are incorporated herein by reference.

BACKGROUND

This invention relates to drive arrangements for robot joints, with particular relevance to robot wrists.

Robots that are required to manipulate objects, which may for example be industrial or surgical robots, frequently have an arm composed of rigid elements which are linked together in series by a number of flexible joints. The joints could be of any type but are typically revolute joints, or a combination of revolute and prismatic joints. The arm extends from a base, whose location might be fixed or moveable, and terminates in a tool or an attachment for a tool. The tool could, for example be a gripping, cutting, illuminating, irradiating or imaging tool. The final joint in the arm may be termed the wrist. The wrist may permit motion about only a single axis, or it may be a complex or compound articulation, which permits rotation about multiple axes. As disclosed in our co-pending patent application PCT/GB2014/053523, the wrist may provide two roll joints whose axes are generally longitudinal to the arm, separated by two pitch/yaw joints, whose axes are generally transverse to the arm.

In the case of a surgical robot there are a number of important criteria that influence the design of the distal joint(s) of the arm.
1. It is desirable for the arm, and particularly its distal portion where the wrist is located, to be small in size. That allows multiple such robot arms to work in close proximity and hence opens up a wider range of surgical procedures that the arm can perform.
2. It is desirable for the outer profile of the distal portion of the arm to be circularly symmetrical about the length of the arm. This allows the distal portion to be rotated longitudinally without having to be repositioned if it is close to another robot, to some other equipment or to the patient.
3. It is desirably for the joints to be capable of delivering a high torque, so that they can carry heavier tools and deliver high acceleration to the tool tip.
4. It is desirable for the joints to be stiff, with little or no backlash or elasticity, so that when a tool tip has been positioned it will be fixed in position. A conventional approach to minimising backlash is to designate one or more gear elements as sacrificial, but this requires a high level of maintenance, and can result in worn gear particles being liberated within the arm.
5. It is desirable for all articulations to have position and force/torque sensors, so that the control mechanism can take data from those sensors.
6. It is desirable for the distal portion of the robot arm to be as light as possible, to reduce the force that must be exerted by more proximal joints of the robot arm.
7. A typical robot arm carries cables that provide power to its drive motors and perhaps to a tool, and carry signals back from sensors such as position, torque and imaging sensors. It is desirable for the arm to include a path for such cables to pass in the interior of the arm.
8. It is desirable for there to be a method of cooling for the motors driving the distal joints of the robot arm and payload or tool.

The number of important criteria makes it difficult to design an arm that best balances all the requirements.

One particular problem is how to fit the motors and gearing into the wrist of a robot arm. The arrangement should be compact but also allow for high stiffness and torque transfer. Many existing designs compromise one of these criteria.

There is a need for an improved drive arrangement for a joint of a robot arm.

SUMMARY

According to the present invention there is provided a robot arm comprising a joint mechanism for articulating one limb of the arm relative to another limb of the arm about two non-parallel rotation axes, the mechanism comprising: an intermediate carrier attached to a first one of the limbs by a first revolute joint having a first rotation axis and to a second one of the limbs by a second revolute joint having a second rotation axis; a first drive gear disposed about the first rotation axis, the first drive gear being fast with the carrier; a second drive gear disposed about the second rotation axis, the second drive gear being fast with the second one of the limbs; a first drive shaft for driving the first drive gear to rotate about the first rotation axis, the first drive shaft extending along the first one of the limbs and having a first shaft gear thereon, the first shaft gear being arranged to engage the first drive gear; a second drive shaft for driving the second drive gear to rotate about the second rotation axis, the second drive shaft extending along the first one of the limbs and having a second shaft gear thereon; and an intermediate gear train borne by the carrier and coupling the second shaft gear to the second drive gear.

The intermediate gear train may comprise a first intermediate gear disposed about the first rotation axis, the first intermediate gear being arranged to engage the second shaft gear. The first intermediate gear may be rotatable about the first rotation axis.

The robot arm may further comprise a control unit arranged to respond to command signals commanding motion of the robot arm by driving the first and second drive shafts to rotate. The control unit may be configured to, when the robot arm is commanded to articulate about the first axis without articulating about the second axis, drive the first shaft to rotate to cause articulation about the first axis and also drive the second shaft to rotate in such a way as to negate parasitic articulation about the second axis. The control unit may be configured to perform that action automatically.

The intermediate gear train may comprise a plurality of interlinked gears arranged to rotate about axes parallel with the first rotation axis.

The intermediate gear train may comprise an intermediate shaft arranged to rotate about an axis parallel with the first rotation axis. The intermediate shaft may have a third shaft gear thereon, the third shaft gear being arranged to engage the second drive gear.

The interlinked gears are on one side of a plane perpendicular to the first axis and containing the teeth of the first drive gear, and at least part of the third shaft gear is on the other side of that plane.

The third shaft gear may be a worm gear: i.e. a gear whose tooth/teeth follow a helical path. One or both of the first and second shaft gears may be worm gears.

One or both of the first drive gears may be bevel gear(s): i.e. gears whose pitch surface is a straight-sided or curved cone and/or whose teeth are arranged on such a cone. The tooth lines may be straight or curved. One or both of the first drive gears may be skew axis gear(s).

The first drive gear may be a part-circular gear. At least part of the second drive gear may intersect a circle about the first axis that is coincident with the radially outermost part of the first drive gear. At least part of the intermediate shaft may intersect a circle about the first axis that is coincident with the radially outermost part of the first drive gear.

According to a second aspect of the present invention there is provided a robot arm comprising a joint mechanism for articulating one limb of the arm relative to another limb of the arm about two non-parallel rotation axes, the mechanism comprising: an intermediate carrier attached to a first one of the limbs by a first revolute joint having a first rotation axis and to a second one of the limbs by a second revolute joint having a second rotation axis; a first drive gear disposed about the first rotation axis, the first drive gear being fast with the carrier; a second drive gear disposed about the second rotation axis, the second drive gear being fast with the second one of the limbs; a first drive shaft for driving the first drive gear to rotate about the first rotation axis, the first drive shaft extending along the first one of the limbs and having a first shaft gear thereon, the first shaft gear being arranged to engage the first drive gear; a second drive shaft for driving the second drive gear to rotate about the second rotation axis, the second drive shaft extending along the first one of the limbs on a first side of a plane containing the second rotation axis and extending through that plane to the second side of that plane; and an intermediate linkage that meshes with the second drive shaft on the second side of the plane and that couples the second shaft gear to the second drive gear.

The second shaft may comprise a flexible element. The flexible element is located on the first rotation axis. The flexible element may be a universal joint.

The second shaft is coupled to the carrier by a revolute joint on the second side of the said plane.

The second drive shaft may have a second shaft gear on the second side of the said plane. The intermediate linkage may comprise an intermediate shaft having a first intermediate gear that meshes with the second shaft gear and a second intermediate gear that meshes with the second drive gear.

The second drive shaft may be arranged to rotate about an axis perpendicular to the second rotation axis.

The second intermediate gear may be a worm gear. The first shaft gear may be a worm gear.

One or both of the first drive gears may be bevel gear(s). One or both of the first drive gears may be skew axis gear(s).

The first drive gear may be a part-circular gear. At least part of the second drive gear may intersect a circle about the first axis that is coincident with the radially outermost part of the first drive gear.

According to a third aspect of the present invention there is provided a robot arm comprising a joint mechanism for articulating one limb of the arm relative to another limb of the arm about two non-parallel rotation axes, the mechanism comprising: an intermediate carrier attached to a first one of the limbs by a first revolute joint having a first rotation axis and to a second one of the limbs by a second revolute joint having a second rotation axis; a first drive gear disposed about the first rotation axis, the first drive gear being fast with the carrier; a second drive gear disposed about the second rotation axis, the second drive gear being fast with the second one of the limbs; a first drive shaft for driving the first drive gear to rotate about the first rotation axis, the first drive shaft extending along the first one of the limbs and having a first shaft gear thereon, the first shaft gear being arranged to engage the first drive gear; a second drive shaft for driving the second drive gear to rotate about the second rotation axis, the second drive shaft extending along the first one of the limbs and having a second shaft gear thereon, the second shaft gear being arranged to engage the second drive gear; the second drive shaft comprising a prismatic joint whereby the length of the shaft can vary in response to motion of the carrier about the first axis.

The prismatic joint may be a sliding splined coupling.

The second dive shaft may comprise a first flexible joint on one side of the prismatic joint and a second flexible joint on the other side of the prismatic joint.

The second drive shaft may be connected by a revolute joint to the carrier on the opposite side of the second flexible joint to the prismatic joint.

One or both of the first and second shaft gears may be worm gears.

One or both of the first drive gears may be bevel gear(s). One or both of the first drive gears may be skew axis gear(s). The first drive gear may be a part-circular gear.

At least part of the second drive gear may intersect a circle about the first axis that is coincident with the radially outermost part of the first drive gear.

The first and second axes may be orthogonal. The first and second axes may intersect each other.

BRIEF DESCRIPTION OF THE DRAWINGS

The present invention will now be described by way of example with reference to the accompanying drawings.

In the drawings.

DETAILED DESCRIPTION

The wrist mechanisms to be described below have been found to provide compact and mechanically advantageous arrangements for at least some of the joints of a robot wrist, or for other applications.

Figure 1:
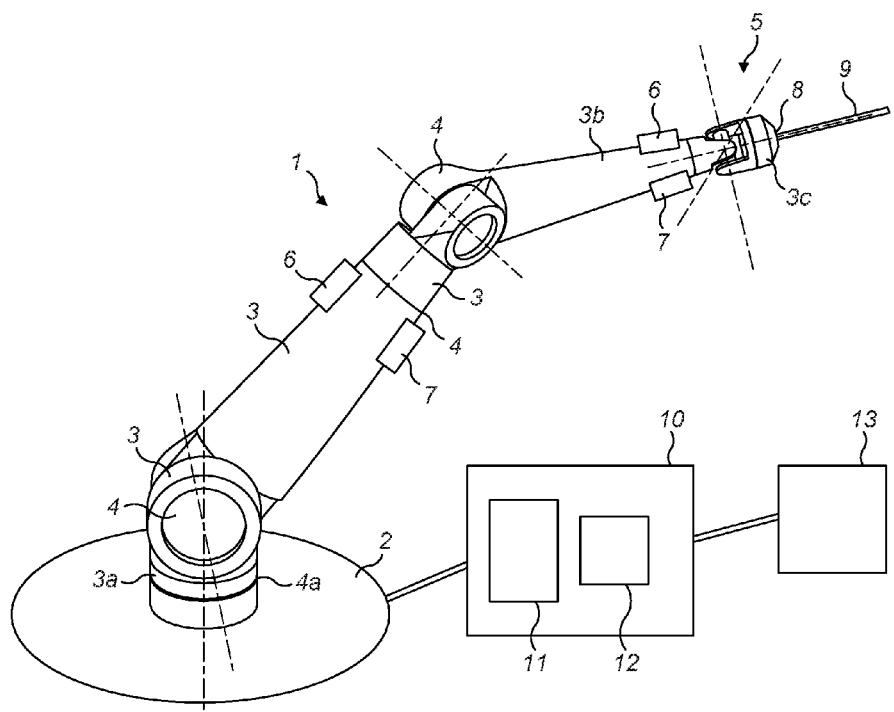
FIG. 1 is a general representation of a surgical robot arm.

FIG. 1 shows a surgical robot having an arm 1 which extends from a base 2. The arm comprises a number of rigid limbs 3. The limbs are coupled by revolute joints 4. The most proximal limb 3a is coupled to the base by joint 4a. It and the other limbs are coupled in series by further ones of the joints 4. A wrist 5 is made up of four individual revolute joints. The wrist 5 couples one limb (3b) to the most distal limb (3c) of the arm. The most distal limb 3c carries an attachment 8 for a surgical instrument or tool 9. Each joint 4 of the arm has one or more motors 6 which can be operated to cause rotational motion at the respective joint, and one or more position and/or torque sensors 7 which provide information regarding the current configuration and/or load at that joint. For clarity, only some of the motors and sensors are shown in FIG. 1. The arm may be generally as described in our co-pending patent application PCT/GB2014/053523. The attachment point 8 for a tool can suitably comprise any one or more of: (i) a formation permitting a tool to be mechanically attached to the arm, (ii) an interface for communicating electrical and/or optical power and/or data to and/or from the tool, and (iii) a mechanical drive for driving motion of a part of a tool. In general it is preferred that the motors are arranged proximally of the joints whose motion they drive, so as to improve weight distribution. As discussed below, controllers for the motors, torque sensors and encoders are distributed with the arm. The controllers are connected via a communication bus to control unit 10.

A control unit 10 comprises a processor 11 and a memory 12. Memory 12 stores in a non-transient way software that is executable by the processor to control the operation of the motors 6 to cause the arm 1 to operate in the manner described herein. In particular, the software can control the processor 11 to cause the motors (for example via distributed controllers) to drive in dependence on inputs from the sensors 7 and from a surgeon command interface 13. The control unit 10 is coupled to the motors 6 for driving them in accordance with outputs generated by execution of the software. The control unit 10 is coupled to the sensors 7 for receiving sensed input from the sensors, and to the command interface 13 for receiving input from it. The respective couplings may, for example, each be electrical or optical cables, or may be provided by a wireless connection. The command interface 13 comprises one or more input devices whereby a user can request motion of the arm in a desired way. The input devices could, for example, be manually operable mechanical input devices such as control handles or joysticks, or contactless input devices such as optical gesture sensors. The software stored in memory 12 is configured to respond to those inputs and cause the joints of the arm to move accordingly, in compliance with a predetermined control strategy. The control strategy may include safety features which moderate the motion of the arm in response to command inputs. Thus, in summary, a surgeon at the command interface 13 can control the robot arm 1 to move in such a way as to perform a desired surgical procedure. The control unit 10 and/or the command interface 13 may be remote from the arm 1.

Figure 2:
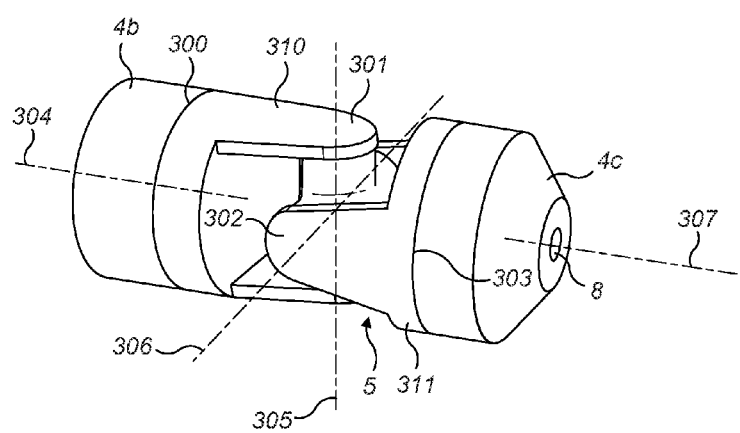
FIG. 2 shows in more detail the rotation axes at the wrist of the arm of FIG. 1.

FIG. 2 shows the wrist 5 of the robot in more detail. The wrist comprises four revolute joints 300, 301, 302, 303. The joints are arranged in series, with a rigid part of the arm extending from each joint to the next. The most proximal joint 300 of the wrist joins arm part 4b to arm part 310. Joint 300 has a "roll" rotation axis 304, which is directed generally along the extent of the limb 4b of the arm that is immediately proximal of the articulations of the wrist. The next most distal joint 301 of the wrist joins arm part 310 to arm part 311. Joint 301 has a "pitch" rotation axis 305 which is perpendicular to axis 304 in all configurations of joints 300 and 301. The next most distal joint 302 of the wrist joins arm part 310 to arm part 311. Joint 302 has a "yaw" rotation axis 306 which is perpendicular to axis 305 in all configurations of joints 301 and 302. In some configurations of the wrist, axis 306 is also perpendicular to axis 304. The next most distal joint of the wrist 303 joins arm part 311 to arm part 4c. Joint 303 has a "roll" rotation axis 307 which is perpendicular to axis 306 in all configurations of joints 302 and 303. In some configurations of the wrist, axis 307 is also perpendicular to axis 305 and parallel with (and preferably collinear with) axis 304. It is preferable for axes 305 and 306 to intersect each other, since this gives a particularly compact configuration. Joints 300 and 303 may be positioned so that axes 304 and 307 can pass through the intersection of axes 305, 306 for some configurations of the wrist.

This design of wrist is advantageous in that it allows a wide range of movement from a tool attached to the attachment point 8 at the distal end of arm part 4c, but with the wrist being capable of being assembled in a relatively compact form and without there being singularities at certain parts of the range of motion that could demand excessively high rates of motion at individual joints.

Figure 3:
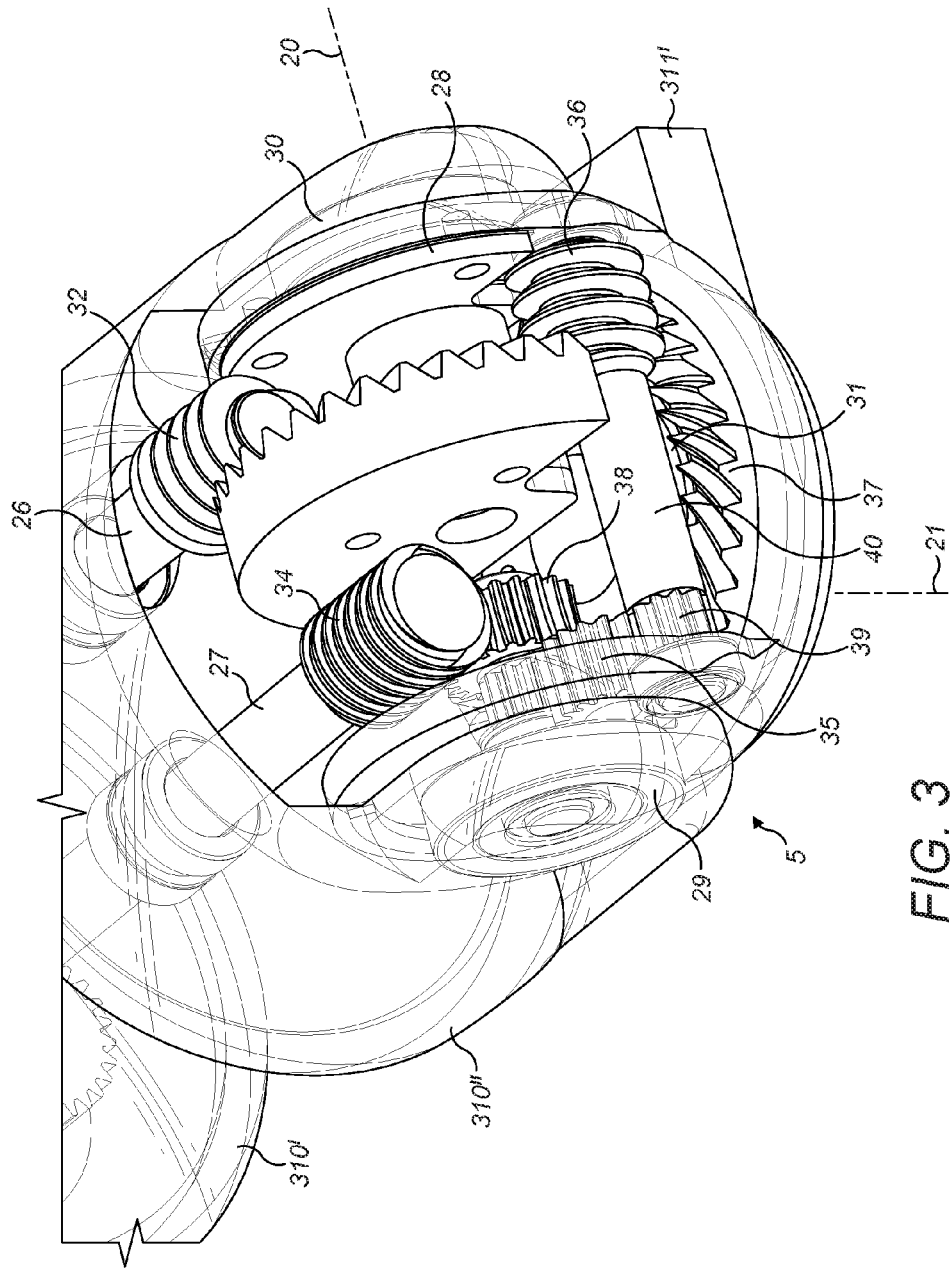
FIG. 3 shows part of a first wrist mechanism from distally and one side.
Figure 4:
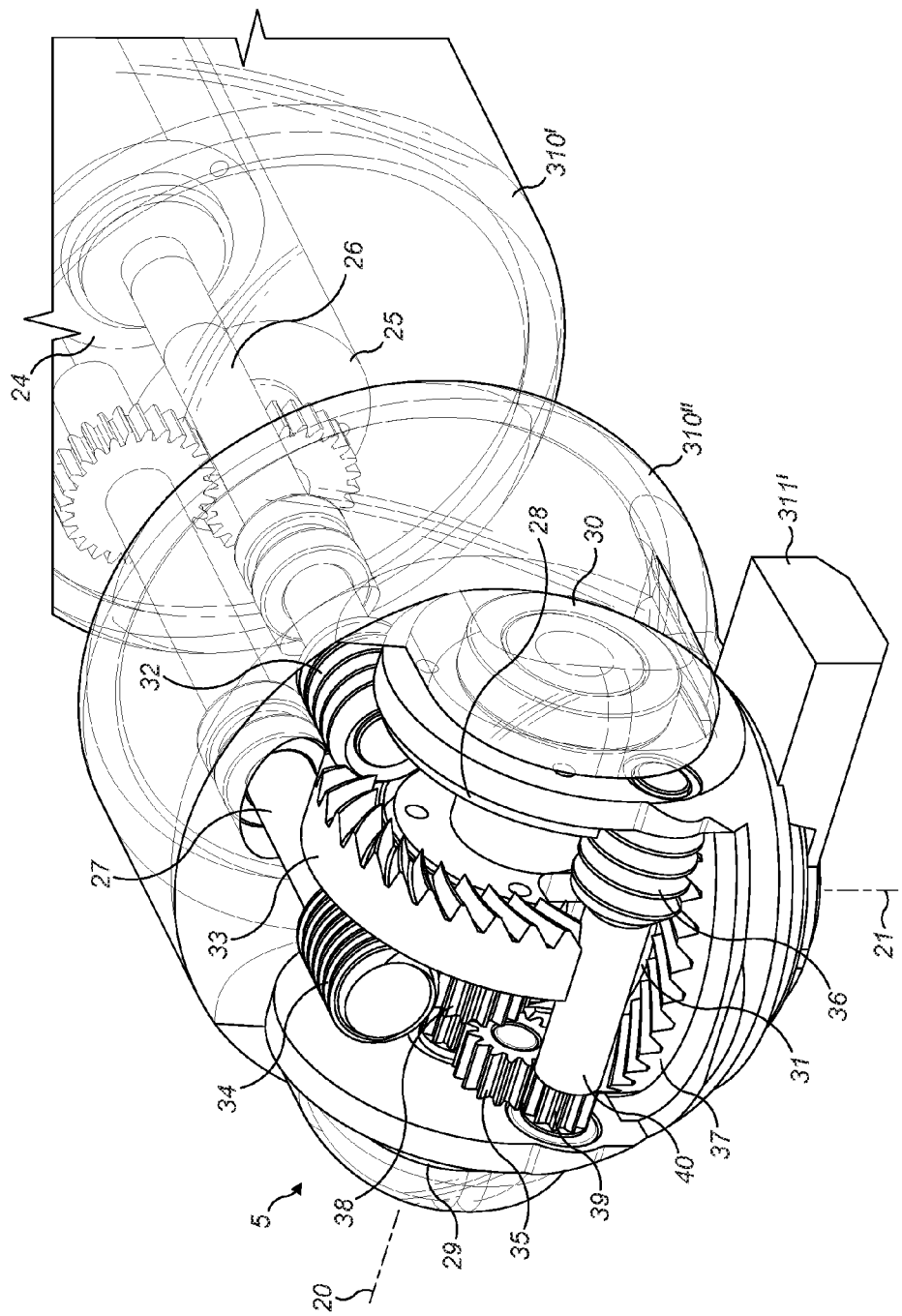
FIG. 4 shows part of the first wrist mechanism from distally and the other side.

FIGS. 3 and 4 show one example of a mechanism suitable for implementing part of the wrist 5 of the arm 1 of FIG. 1. FIGS. 3 and 4 concentrate (as to FIGS. 5 to 10) on the mechanism associated with the joints designated 301 and 302 in FIG. 2.

In the region of the wrist 5 the rigid arm parts 310, 311 have hollow outer shells or casings 310', 310", 311'. The shells define the majority of the exterior surface of the arm, and include a void which is partly or fully encircled by the exterior wall of the respective shell and within which the motors, sensors, cables and other components of the arm can be housed. The shells could be formed of a metal, for example an aluminium alloy or steel, or from a composite, for example a fibre-reinforced resin composite such as carbon fibre reinforced resin. The shells constitute part of the rigid structure of the arm parts that attaches between the respective joints. The shells may contain a structural framework as shown later in relation to the embodiment of FIG. 7.

In FIGS. 3 and 4, for clarity the shell of arm part 310 is shown in two parts: 310' and 310", both of which are drawn in outline and exploded from each other. The shells of arm parts 4b and 4c are omitted, as is the mechanism associated with joints 300 and 303. The shell of arm part 311 is shown in part, the majority extending from spur 311'.

The shell of arm part 310 (constituted by shell parts 310' and 310") and the shell of arm part 311 (which extends from spur 311') are movable with respect to each other about two rotation axes, shown at 20 and 21. These correspond to axes 305, 306 of FIG. 2. Axes 20 and 21 are orthogonal. Axes 20 and 21 intersect. A central coupler 28 is mounted to arm part 310 by bearings 29, 30. The coupler extends between the bearings 29, 30. The bearings 29, 30 hold the coupler fast with arm part 310 except that they permit relative rotation of the coupler and that arm part about axis 20, thus defining a revolute joint corresponding to joint 301 of FIG. 2. A further bearing 31 attaches the distal shell connector spur 311' to the coupler 28. Bearing 31 holds the distal shell connector spur 311' fast with the coupler 28 except for permitting relative motion of the spur and the coupler about axis 21, thus defining a revolute joint corresponding to joint 302 of FIG. 2.

Thus coupler 28 is fast with the arm part 310 about axis 21. Coupler 28 is also fast with the arm part 311 about axis 20. That is, the mechanism is arranged so that coupler 28 and arm part 310 cannot undergo relative rotation or motion about axis 21; and coupler 28 and arm part 311 cannot undergo relative rotation or motion about axis 20.

Two electric motors 24, 25 (see FIG. 4) are mounted in arm part 310. The motors drive respective drive shafts 26, 27 which extend into the midst of the wrist mechanism. Shaft 26 drives rotation about axis 20. Shaft 27 drives rotation about axis 21. Drive shaft 26 terminates at its distal end in a worm gear 32. The worm gear 32 engages a bevel gear 33 which is fast with the coupler 28. Drive shaft 27 terminates at its distal end in a worm gear 34. The worm gear 34 engages a gear train shown generally at 35 which terminates in a further worm gear 36. Worm-form pinion gear 36 engages a hypoid-toothed bevel gear 37 which is fast with the distal shell connector 311'.

In this example, the gear 33 is directly attached to the coupler 28. That is, the coupler 28 abuts the gear 33. Gear 33 is therefore mounted to the coupler 28. The distal shell connector spur 311' is also directly attached to the gear 37. Thus the gear 37 may abut the connector spur 311'.

Shafts 26 and 27 are parallel. They both extend along the arm part 310. In particular, shafts 26 and 27 extend in a direction substantially parallel to the longitudinal direction of the arm part 310. The shafts could be parallel to the longitudinal direction of the arm part 310, or they could be mounted at an angle to the general longitudinal direction of the arm part 310. For example, the arm part 310 may taper in the direction from the proximal end towards the distal end, and the shafts 26 and 27 may extend in a direction that is parallel to the taper angle of the arm part.

Worms 32 and 34 are attached to the drive shafts 26 and 27 respectively and so may be referred to as shaft gears. Rotation of gear 33 drives rotation of arm part 311 relative to arm part 310 about axis 20, and thus gear 33 may be referred to as a drive gear. Similarly, rotation of gear 37 drives rotation of arm part 311 relative to arm part 310 about axis 21, and thus gear 37 may also be referred to as a drive gear.

Gear 33 is formed as a sector gear: that is its operative arc (defined in the example of FIGS. 3 and 4 by the arc of its teeth) is less than 360°.

The gear train 35 is borne by the coupler 28. The gear train comprises an input gear 38 which engages the worm 34. Input gear 38 is located with its rotation axis relative to the coupler 28 being coincident with axis 20. That means that the input gear can continue to engage the worm 34 irrespective of the configuration of the coupler 28 relative to arm part 310 about axis 20. A series of further gears whose axes are parallel with axis 20 transfer drive from the input gear 38 to an output gear 39 on a shaft 40 whose rotation axis relative to the carrier 28 is parallel with but offset from axis 20. Shaft 40 terminates in the worm 36. Shaft 40 extends parallel to axis 20. The gears of gear train 35, together with shaft 40, are borne by the coupler 28.

The operation of the wrist mechanism will now be described. For motion about axis 20, motor 24 is operated to drive shaft 26 to rotate relative to arm part 310. This drives the bevel gear 33 and hence coupler 28 and distal shell spur 311' to rotate about axis 20 relative to arm part 310. For motion about axis 21, motor 25 is operated to drive shaft 27 to rotate relative to arm part 310. This drives the bevel gear 37 and hence distal shell connector 311' to rotate about axis 21 relative to arm part 310. It will be observed that if drive shaft 26 is rotated, driving the coupler 28 to rotate, whilst drive shaft 27 remains stationary then gear 38 will also rotate relative to the coupler 28, causing parasitic motion of the distal shell connector spur 311' about axis 21. To prevent this, the control system 10 of the arm is configured so that when required there is compensatory motion of drive shaft 27 in tandem with motion of drive shaft 26 so as to isolate motion about axis 21 from motion about axis 20. For example, if it is required to cause relative motion of shells 310, 311 about only axis 20 then motor 24 is operated to cause that motion whilst motor 25 is simultaneously operated in such a way as to prevent input gear 38 from rotating relative to carrier 28.

Various aspects of the mechanism shown in FIGS. 3 and 4 are advantageous in helping to make the mechanism particularly compact.

1. It is convenient for bevel gear 33 to be of part-circular form: i.e. its teeth do not encompass a full circle. For example, gear 33 may encompass less than 270° or less than 180° or less than 90°. This allows at least part of the other bevel gear 37 to be located in such a way that it intersects a circle coincident with gear 33, about the axis of gear 33 and having the same radius as the outermost part of gear 33. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 20 is restricted.

2. It is convenient if the part gear 33 serves rotation about the axis 20 by which the carrier 28 is pivoted to the next-most-proximal arm part 310, as opposed to rotation about axis 21, since the part gear can also be cut away to accommodate shaft 40 intersecting the said circle. That saves space by permitting the worm 36 to be located on the opposite side of bevel gear 33 to the gear train 35. However, in other designs the part gear could serve rotation about axis 21, so gear 37 could be of part-circular form.

3. It is convenient if the worms 32, 34 are located on the opposite side of axis 20 to bevel gear 37: i.e. that there is a plane containing axis 20 on one side of which are the worms 32, 34 and on the other side of which is the bevel gear 37. This helps to provide a compact packaging arrangement. Thus, both worms 32 and 34 are located on a single side of a plane containing axis 20 that is parallel to the longitudinal direction of the arm part 310.

4. It is convenient if the worm 34 is located on the opposite side of bevel gear 33 from worm 36 and/or that the gear train 35 is located exclusively on the opposite side of bevel gear 33 from worm 36. This again helps to provide a compact packaging arrangement. That is, the gear train 35 (including all its interlinked gears such as gears 38 and 39) may be located on one side of the gear 33. Put another way, gear train 35 (including its interlinked gears) and the gear 33 are located on opposite sides of a plane parallel to both axis 21 and the longitudinal direction of arm part 310. That plane may contain the axis 21.

5. The gears 33 and/or 37 are conveniently provided as bevel gears since that permits them to be driven from worms located within the plan of their respective external radii. However, they could be externally toothed gears engaged on their outer surfaces by the worms 32, 34 or by radially toothed gears.

6. The bevel gear 33 is conveniently located so as to be interposed between worms 32 and 34. This helps the packaging of the motors 24, 25.

7. The bevel gears and the worm gears that mate with them can conveniently be of hypoid or skew axis, e.g. Spiroid®, form. These gears allow for relatively high torque capacity in a relatively compact form.

Figure 5:
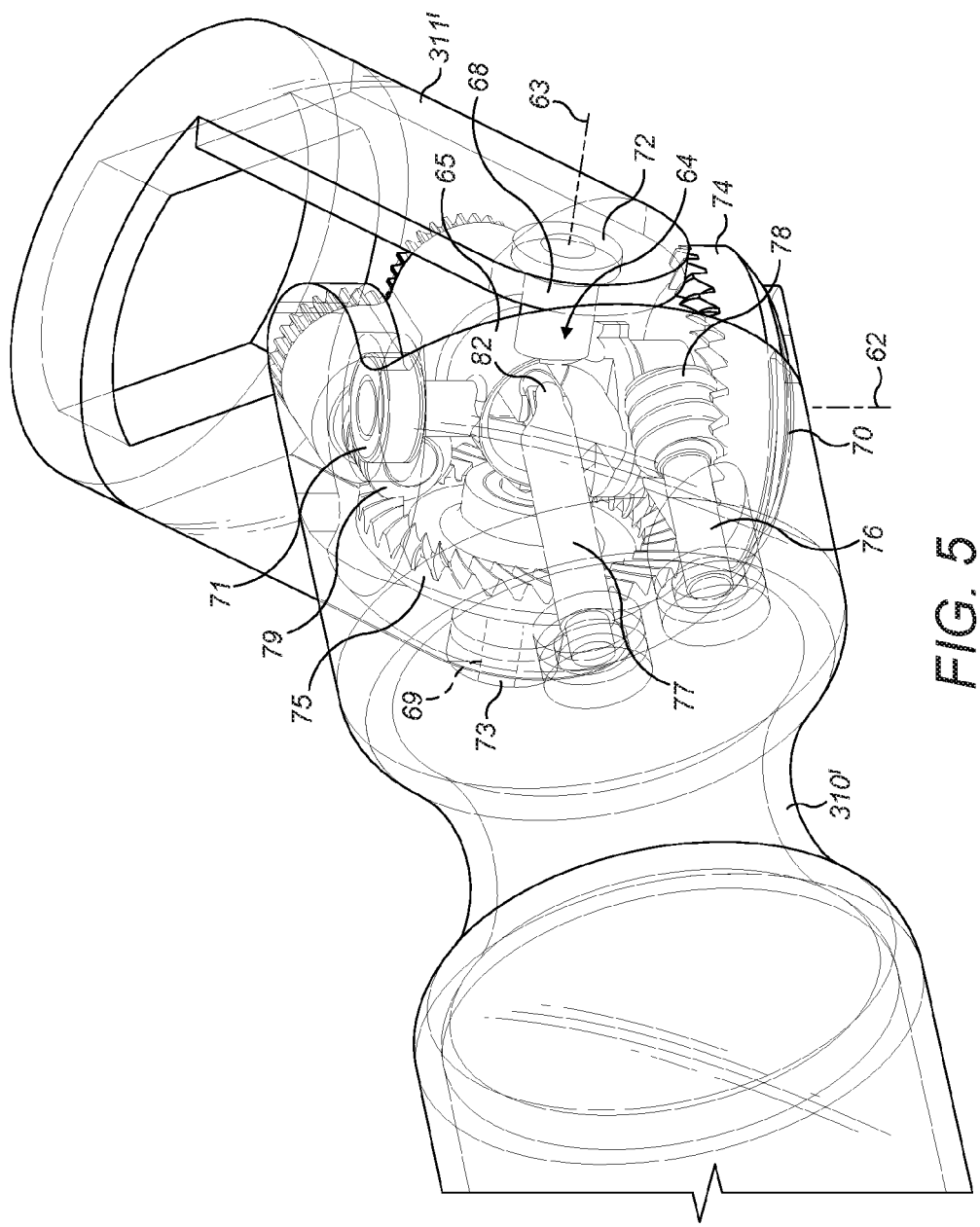
FIG. 5 shows part of a second wrist mechanism from proximally and one side.
Figure 6:
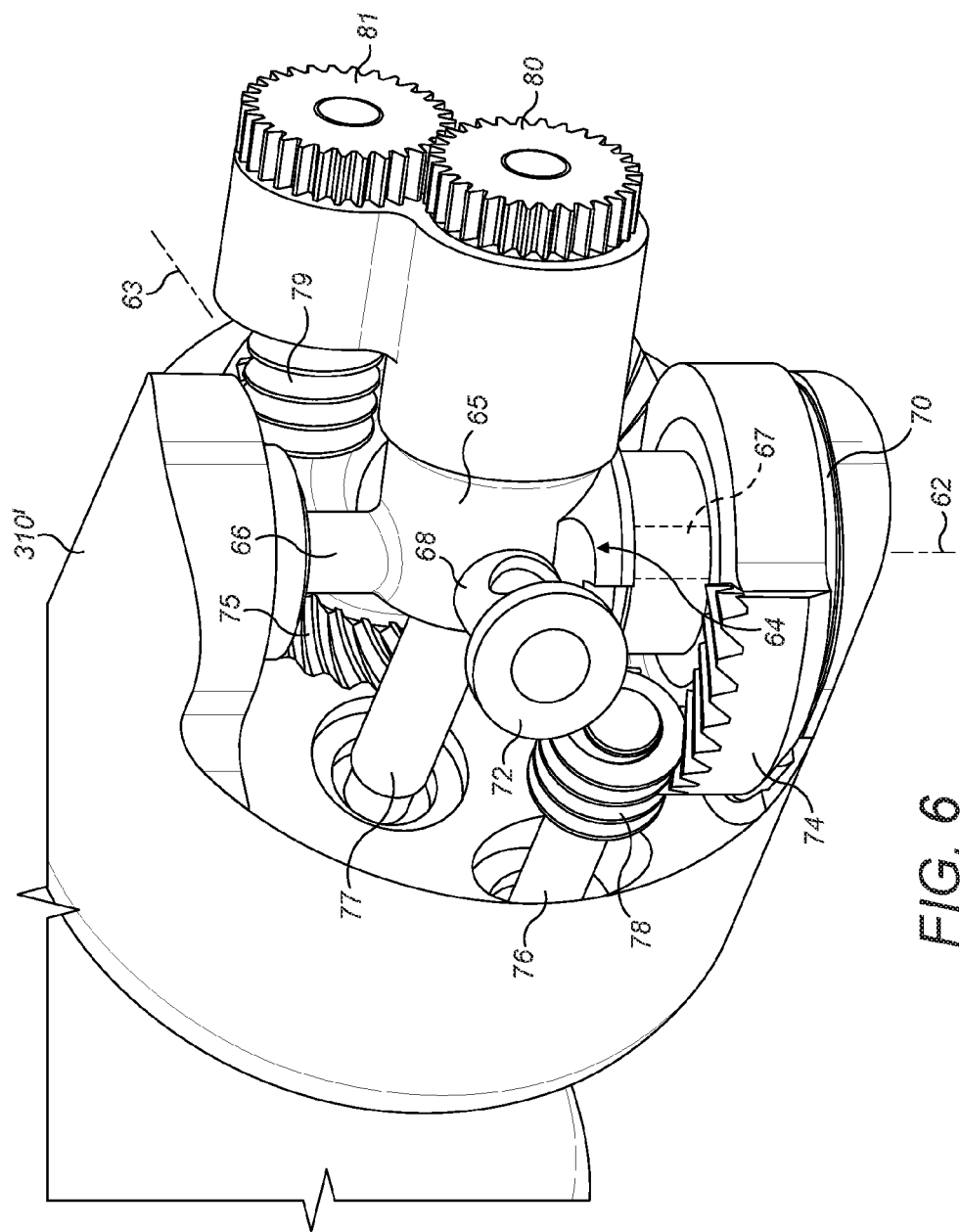
FIG. 6 shows part of the second wrist mechanism from distally and one side.
Figure 7:
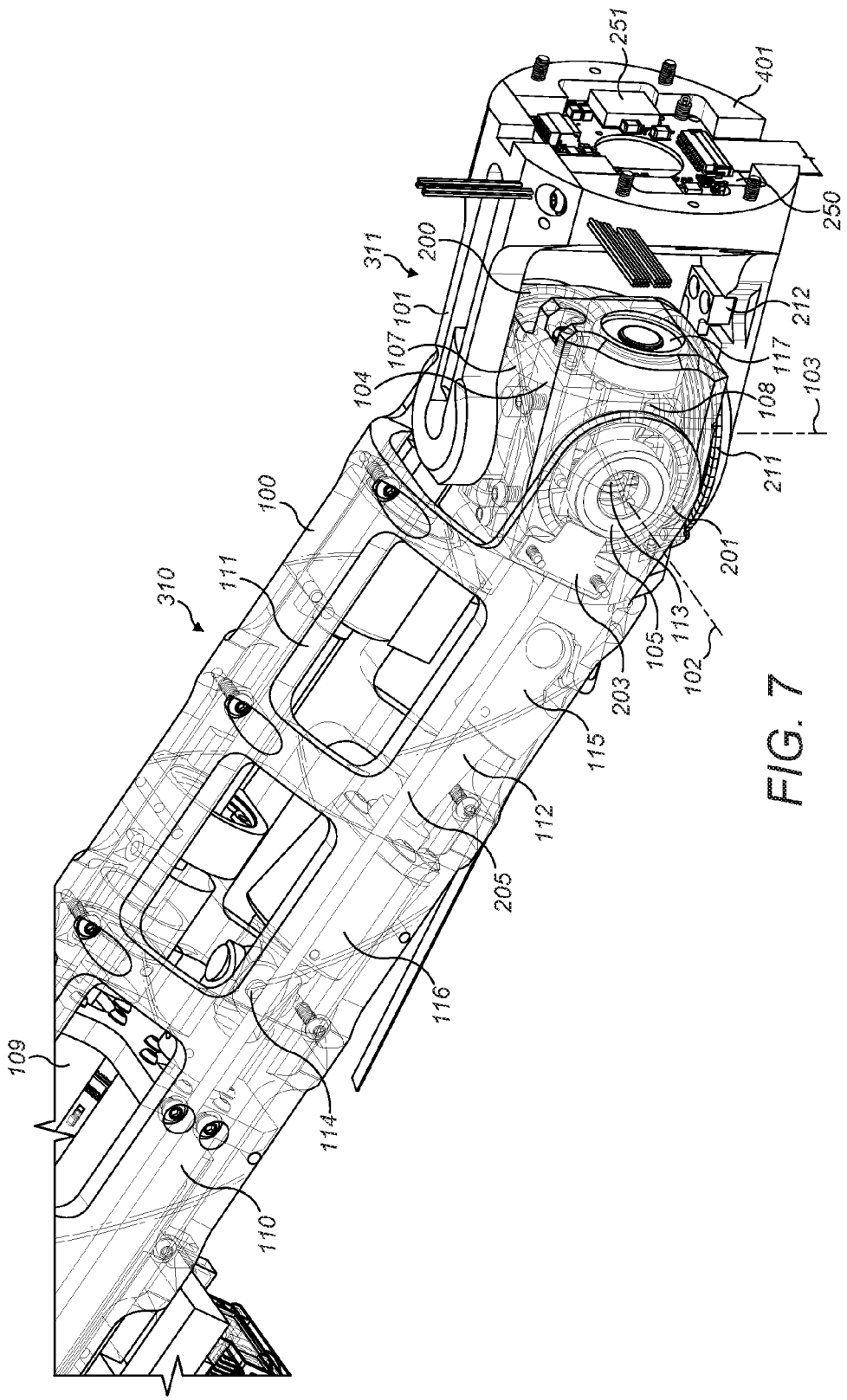
FIG. 7 shows a third wrist mechanism from distally and one side.
Figure 8:
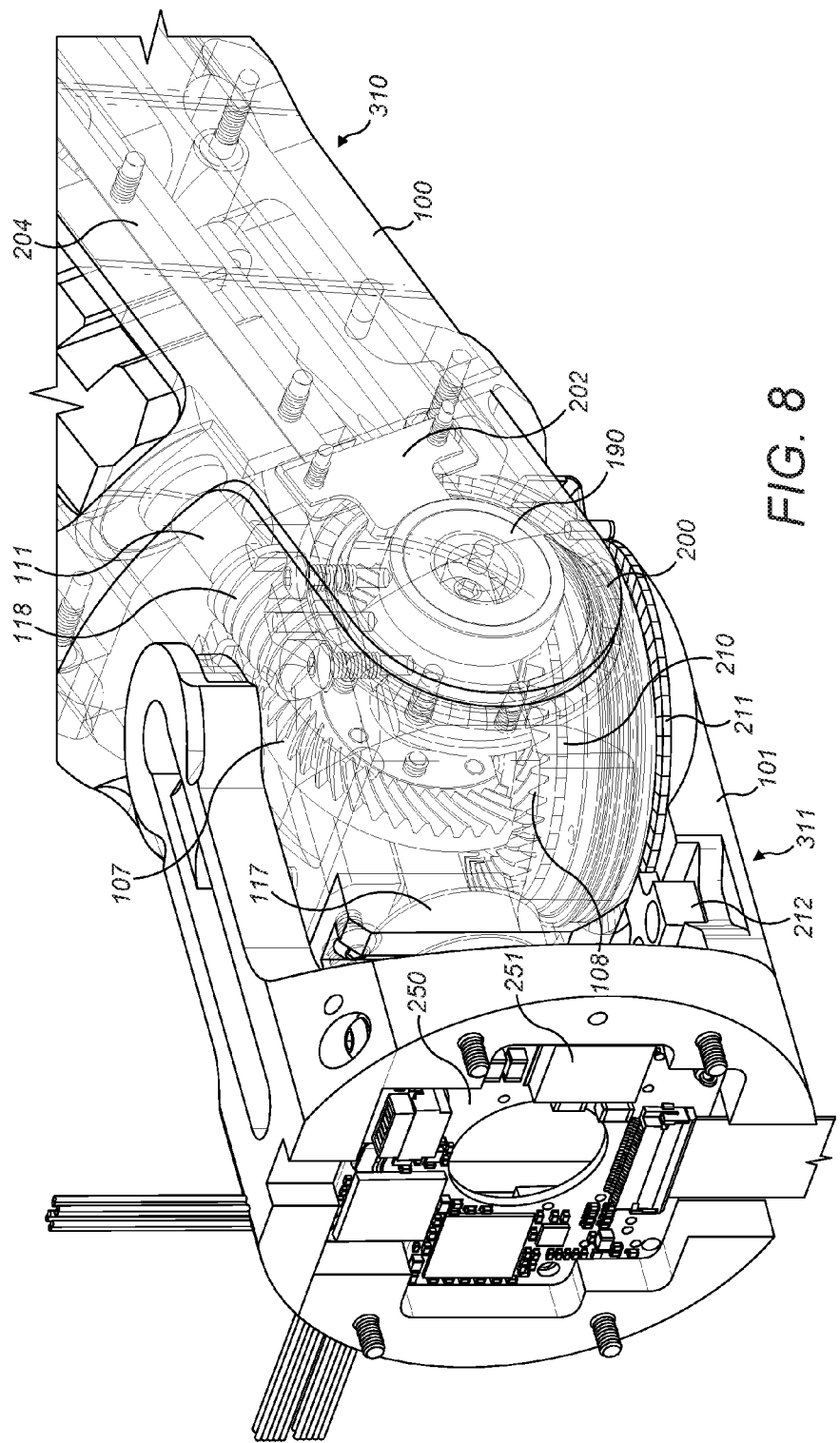
FIG. 8 shows the third wrist mechanism from distally and the other side.

FIGS. 5 and 6 show a second form of wrist mechanism suitable for providing joints 301, 302 in a wrist of the type shown in FIG. 2.

As shown in FIG. 5 the wrist comprises a pair of rigid external shells 310', 311' which define the exterior surfaces of arm parts 310, 311 respectively of FIG. 2. 310' is the more proximal of the shells. The arm parts formed of the shells 310', 311' can pivot relative to each other about axes 62, 63, which correspond respectively to axes 305, 306 of FIG. 2. Axes 62, 63 are orthogonal. Axes 62, 63 intersect. The shells 310', 311' define the exterior of the arm in the region of the wrist and are hollow, to accommodate a rotation mechanism and space for passing cables etc., as will be described in more detail below. The shells could be formed of a metal, for example an aluminium alloy or steel, or from a composite, for example a fibre-reinforced resin composite such as carbon fibre. The shells constitute the principal rigid structure of the arm parts that attaches between the respective joints.

FIG. 6 shows the same mechanism from distally and one side, with the shell 311' removed for clarity.

Shell 310' is coupled to shell 311' by a cruciform coupler 64. The coupler has a central tube 65 which defines a duct through its centre, running generally along the length of the arm. Extending from the tube are first arms 66, 67 and second arms 68, 69. Each of the shells 310', 311' is attached to the coupler 64 by a revolute joint: i.e. in such a way that it is confined to be able to move relative to the coupler only by rotation about a single axis. The first arms 66, 67 attach to shell 310' by bearings 70, 71 which permit rotation between those first arms and the shell 310' about axis 62. The second arms 68, 69 attach to shell 311' by bearings 72, 73 which permit rotation between those second arms and the shell 311' about axis 63. A first bevel gear 74 is concentric with the first arms 66, 67. The first bevel gear is fast with the coupler 64 and rotationally free with respect to the proximal one of the two shells 310'. A second bevel gear 75 is concentric with the second arms 68, 69. The second bevel gear is fast with the distal one of the two shells 311' and rotationally free with respect to the coupler 64.

The pair of arms 66, 67 of the coupler are perpendicular to the pair of arms 68, 69. Arms 66 and 67 lie on the rotation axis 62; and arms 68 and 69 lie on the rotation axis 63. The coupler 64 is directly attached to the gear 74. Thus the coupler 64 abuts gear 74. Coupler 64 (and hence gear 74) can rotate relative to the arm part 310 about axis 62. However, the coupler 64 and gear 74 are fast with the arm part 310 about the axis 63 such that there can be no relative motion or rotation between the coupler 64 and arm part 310 about axis 63.

The bevel gear 75 may be mounted directly to the arm part 311. The bevel gear 75 can rotate with respect to the coupler 64 (and hence arm part 310) about axis 63. However, the gear 75 is fast with the coupler 64 about axis 62. That is, there can be no relative rotation or motion between coupler 64 and gear 75 about axis 62.

Two shafts 76, 77 operate the motion of the compound joint. The shafts extend into the central region of the joint from within the proximal one of the shells 310'. Each shaft is attached at its proximal end to the shaft of a respective electric motor (not shown), the housings of the motors being fixed to the interior of the proximal shell 310'. In this way the shafts 76, 77 can be driven by the motors to rotate with respect to the proximal shell 310'.

Shaft 76 and its associated motor operate motion about axis 62. Shaft 76 terminates at its distal end in a worm gear 78 which engages bevel gear 74. Rotation of shaft 76 causes rotation of the bevel gear 74 relative to shell 310' about axis 62. Bevel gear 74 is fast with the coupler 64, which in turn carries the distal shell 311'. Thus rotation of shaft 76 causes relative rotation of the shells 310', 311' about axis 62.

Shaft 77 and its associated motor operate motion about axis 63. In order to do that it has ultimately to drive bevel gear 75 by means of a worm gear 79 carried by the coupler 64. Rotation of that worm gear can cause relative rotation of the coupler and the distal shell 311'. To achieve this, drive is transmitted from the shaft 77 through a pair of gears 80, 81 borne by the carrier 64 to a shaft bearing the worm gear 79. Shaft 77 approaches the carrier 64 from the proximal side. The gears 80, 81 are located on the distal side of the coupler. Gears 80, 81 and 79 are thus fast with the coupler 64 about axes 62 and 63. The shaft 77 passes through the duct defined by tube 65 in the centre of the coupler. To accommodate motion of the coupler 64 relative to the first shell 310' the shaft 77 has a universal or Hooke's joint 82 along its length. The universal joint 82 lies on axis 62. Instead of a Hooke's joint the shaft could have another form of flexible coupling, for example an elastic coupling (which could be integral with the shaft) or a form of constant velocity joint.

Worm 78 is attached to drive shaft 76 and so may be referred to as a shaft gear. Rotation of gear 74 drives rotation of the arm part 311 relative to the arm part 310 about axis 62, and thus gear 74 may be referred to as a drive gear. Similarly, rotation of gear 75 drives rotation of arm part 311 relative to arm part 310 about axis 63, and so gear 75 may also be referred to as a drive gear.

Shaft 77 traverses a plane that contains rotation axis 63. The plane additionally contains rotation axis 62. Thus the shaft 77 comprises a proximal portion that is proximal of that plane, and a distal portion that is distal of that plane. The proximal portion of the shaft 77 is attached or otherwise coupled to the motor. The distal portion of the shaft attaches to the gear 80. Gear 80 is therefore located on the distal side of that plane. Gear 80 may also be referred to as a shaft gear. The proximal and distal portions of the shaft 77 may be separated by the Hooke's joint 82. The Hooke's joint permits the proximal and distal portions of the shaft 77 to rotate with each other such that rotation of the proximal portion is coupled to the distal portion. Since the distal portion of shaft 77 is attached to gear 80, it follows that gear 80 is rotationally fast with shaft 77.

Gear 80 engages, or meshes with, gear 81. In this example gears 80 and 81 are spur gears. Gears 80 and 81 have parallel but offset rotation axes. The rotation axis of gear 80 is collinear with the rotation axis of the distal portion of shaft 77. Worm 79 is arranged to rotate in response to a rotation of gear 81. Worm 79 may be rotationally fast with gear 81 such that a rotation of gear 81 causes a corresponding rotation of worm 79. Worm 79 may have a rotation axis that is collinear with the rotation axis of gear 81. Thus gears 80 and 81 operate to couple rotation of shaft 77 to rotation of gear 79 about a rotation axis parallel to the rotation axis of the distal portion of shaft 77.

The rotation axis of worm 79 is not parallel and does not intersect the rotation axis of gear 75 (axis 63). Gear 75 is therefore a skew-axis gear. Similarly, the rotation axes of worm 78 and gear 74 are non-parallel and non-intersecting. Thus gear 74 is also a skew-axis gear.

It is observed that rotation of the shaft 76, which causes the coupler 64 to rotate about axis 62, may cause gears 80 and 81 (and thus worm gear 79) to rotate when the shaft 77 is held stationary, causing parasitic motion of the distal shell 311' relative to the shell 310' about the rotation axis 63. This is because the rotation of the coupler 64 about axis 62 driven by the rotation of the shaft 77 needs to be accommodated by the Hooke's joint 82, and that rotation of the coupler 64 may cause a parasitic rotation of the Hooke's joint about the longitudinal axis of the shaft 77. Any such parasitic rotation of the Hooke's joint may cause a consequent rotation of gears 80 and 81, and thus rotation of the bevel gear 75. Such parasitic motion may be prevalent if the hinge axes of the Hooke's joint are not perpendicular to each other, and/or if one of the hinge axes is not parallel and coincident with the rotation axis 62.

To prevent this parasitic motion, the control system 10 may be configured to drive compensatory motion of the shaft 77 in tandem with motion of the shaft 76 so as to isolate motion about axis 62 from motion about axis 63. Thus the control system 10 may be arranged to operate the motor to drive rotation of shaft 76 to cause rotation of arm part 311' relative to arm part 310' about axis 63 whilst simultaneously operating the motor to drive shaft 77 to rotate in such a way as to prevent parasitic rotation about axis 63. The control system 10 may be configured to operate in this manner when the robot arm is commanded to articulate about axis 62 without articulating about axis 63.

The control system 10 may also be configured to drive rotation of shafts 76 and/or 77 in such a way as to reduce irregularities (i.e. increase smoothness) in the rotation of the Hooke's joint 82. The Hooke's joint may experience irregularities in its rotation when it is off axis, i.e. when arm part 311' is pitched relative to arm part 310' about axis 62. Thus when the arm part 311' is commanded to articulate relative to arm part 310' about axis 63 when arm part 311' is pitched relative to arm part 310' about axis 62, the control system may operate to drive the rotation of shaft 77 in such a way as to maintain a smooth or consistent rotation speed of the Hooke's joint 82. This may help to provide a smooth and/or consistent rotation about axis 63.

This mechanism has been found to be capable of providing a particularly compact, light and rigid drive arrangement for rotation about axes 62 and 63 without the components of the mechanism unduly restricting motion of the shells. It permits both motors to be housed in the proximal shell which reduces distal weight.

Various aspects of the mechanism shown in FIGS. 5 and 6 are advantageous in helping to make the mechanism particularly compact.

1. It is convenient for bevel gear 74 to be of part-circular form: i.e. its teeth do not encompass a full circle. For example, gear 74 may encompass less than 270° or less than 180° or less than 90°. This allows at least part of the other bevel gear 75 to be located in such a way that it intersects a circle coincident with gear 74, about the axis of gear 74 and having the same radius as the outermost part of gear 74. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 62 is restricted. As shown in FIG. 6, the bevel gear 74 is of reduced radius in the region not encompassed by its teeth. Part-circular bevel gears of the other embodiments may be formed in the same manner.

2. The gears 74 and/or 75 are conveniently provided as bevel gears since that permits them to be driven from worms located within the plan of their respective external radii. However, they could be externally toothed gears engaged on their outer surfaces by the worms 76, 79, or by radially toothed gears.

4. The bevel gears and the worm gears that mate with them can conveniently be of skew axis, e.g. Spiroid®, form. These allow for relatively high torque capacity in a relatively compact form.

FIGS. 7 to 10 illustrate another form of wrist mechanism. In these figures the shells of arm parts 310, 311 are omitted, exposing the structure within the arm parts.

Proximal arm part 310 has a structural framework 100, which is shown in outline in some of the figures. Distal arm part 311 has a structural framework 101. Arm parts 310 and 311 are rotatable relative to each other about axes 102, 103, which correspond to axes 305, 306 respectively of FIG. 2. A carrier 104 couples the arm parts 310, 311 together. Carrier 104 is attached by bearings 105, 190 to arm part 310. Those bearings define a revolute joint about axis 102 between arm part 310 and the carrier 104. Carrier 104 is attached by bearing 106 to arm part 311. Those bearings define a revolute joint about axis 103 between arm part 311 and the carrier 104. A first bevel gear 107 about axis 102 is fast with the carrier 104. A second bevel gear 108 about axis 103 is fast with arm part 311.

The carrier 104 can therefore rotate relative to the arm part 310 about axis 102. However, the carrier 104 is otherwise fast with the arm part 310 and in particular is fast about axis 103. Thus the carrier 104 is not permitted to undergo relative rotation with respect to arm part 310 about axis 103. The second bevel gear 108 can rotate relative to the carrier 104 about axis 103. The second bevel gear 108 (and hence the arm part 311) may be fast with the carrier about axis 102. Thus the second bevel gear 108 is permitted to undergo relative rotation with respect to the carrier 104 about axis 103 but is not permitted to undergo relative rotation with respect to the carrier about axis 102.

Axes 102 and 103 are in this example perpendicular, but in general are two non-parallel axes. They may be substantially orthogonal to each other. The axes are substantially transverse to the longitudinal direction of the arm part 310 in at least one configuration of the joints 301 and 302. In the arrangement shown, one such configuration is when arm part 311 is not articulated with respect to arm part 310. In the context of a Cartesian coordinate system. Axis 102 may be considered as a "pitch" rotation axis and axis 103 as a "yaw" rotation axis.

As with the other mechanisms described herein, the carrier 104 is located inboard of the limbs 310, 311.

Two motors 109, 110 are fixed to the framework 100 of arm part 310. Motor 109 drives a shaft 111. Shaft 111 is rigid and terminates in a worm 118 which engages bevel gear 107. When motor 109 is operated, shaft 111 rotates relative to the proximal arm part 310, driving bevel gear 107 and hence coupler 104 and arm part 311 to rotate relative to arm part 310 about axis 102. Motor 110 drives a shaft 112. Shaft 112 has a worm 113 near its distal end which engages bevel gear 108. To accommodate motion of bevel gear 108 relative to motor 110 when the coupler 104 moves about axis 102 shaft 112 includes a pair of universal joints 114, 115 and a splined coupler 116 which accommodates axial extension and retraction of shaft 112. The final part of shaft 112 is mounted to the coupler 104 by bearing 117.

The splined coupler 116 is an example of a prismatic joint.

Figure 10:
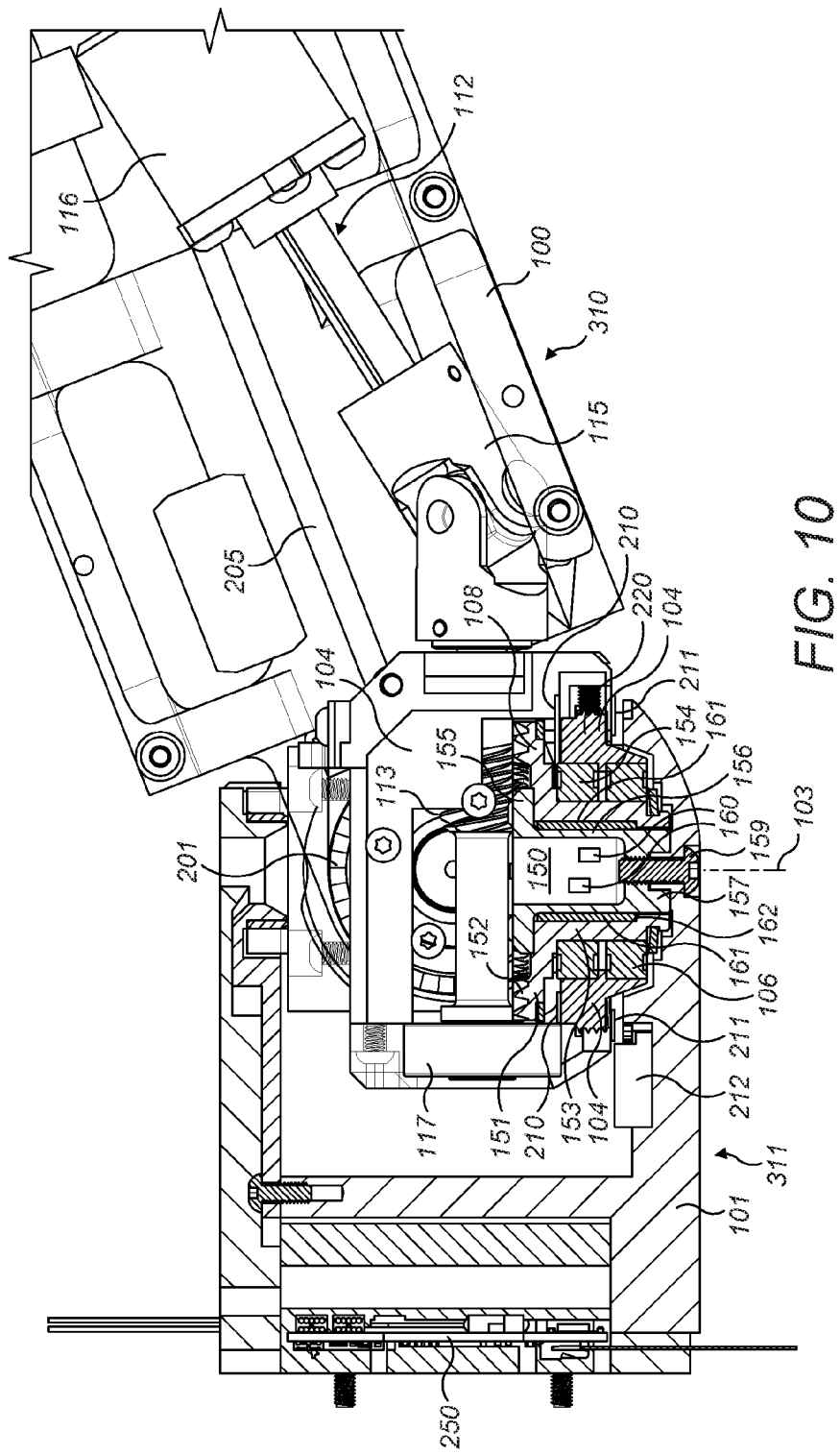
FIG. 10 shows the third wrist mechanism in section on a central longitudinal plane viewed from the other side.

The distal part of the shaft 112 that is mounted to the carrier 104 by bearing 117 is fast with the worm 113 (shown most clearly in FIG. 10). The bearing 117 defines a revolute joint located on the opposite side of the universal joint 115 to the coupler 116. This revolute joint permits the distal part of the shaft 112 to rotate relative to the carrier 104. The distal part of the shaft 112 extends in a direction perpendicular to the axis 102 in all rotational positions of the carrier, and is rotatable with respect to the carrier 104 about an axis perpendicular to axis 102. It can be seen with reference to FIG. 7 that the shaft 112 traverses a plane containing axis 102 that is transverse to the longitudinal direction of the arm part 310. In this example the distal part of the shaft 112 is directly attached to the worm 113 and so extends between the worm and the carrier 104. The distal part of the shaft 112 is mounted to the carrier 104 so as to securely engage the worm 113 with the bevel gear 108 when the carrier 104 is articulated about the axis 102.

The universal joints 114 and 115 of shaft 112 are located on opposing sides of the coupler 116. Both universal joints are located proximally of the rotation axes 102 and 103. The universal joints 114, 115 and the coupler 116 are arranged to permit the carrier 104 to rotate relative to arm part 310 about axis 102.

Bevel gear 107 is disposed about axis 102. That is, gear 107 has as its rotation axis the axis 102. The rotation of gear 107 about axis 102 drives rotation of the arm part 311 relative to the arm part 310. Gear 107 may therefore be referred to as a drive gear.

Bevel gear 108 is disposed about axis 103. Thus bevel gear 108 has as its rotation axis the axis 103. The rotation of gear 108 about axis 103 drives rotation of the arm part 311 relative to the arm part 310 about axis 310. Gear 108 may therefore also be referred to as a drive gear.

Shaft 111 extends along the longitudinal direction of the arm part 310. The longitudinal axis of shaft 111 may be perpendicular to axis 102 in all rotational positions of the carrier 104 about axes 102 and 103. The shaft 111 (and the affixed worm 118) rotate about the longitudinal axis of the shaft 111. This rotation axis is non-parallel and non-intersecting with the rotational axis 102 of the gear 107. Gear 107 is therefore a skew axis gear.

Both worms 113 and 118 may be located on a single side of a plane containing axis 103 that is transverse to the longitudinal direction of the arm part 311 when that arm part is aligned with arm part 310 about axis 103, in other words when arm part 311 is not in yaw relative to arm part 310. In particular, both worms may be located on the proximal side of that plane. However, the worms 113 and 118 may be located on opposing sides of a plane containing axis 102 that is parallel to the longitudinal direction of the arm part 311.

Due to the operation of the universal joints 114 and 115 and the coupler 116, the worm gears 113 and 118 undergo rotation with respect to each other about axis 102 when the carrier 104 is articulated about axis 102. When arm part 310 is aligned with arm part 311 about axis 102 (i.e., when arm part 311 is not in pitch relative to arm part 310), then worm gear 113 and the distal part of shaft 112 are parallel to worm gear 118 and shaft 111. In all other configurations of the arm parts about axis 102, worm gear 113 and the distal part of shaft 112 are non-parallel to worm gear 118 and shaft 111.

Worms 113 and 118 are each attached to respective drive shafts 112 and 111 and so may be referred to as shaft gears.

Operation of the joint mechanism will now be described.

To drive articulations about axis 102, motor 109 is operated to rotate the drive shaft 111 about its longitudinal axis. Because the shaft gear 118 is attached to the shaft 111, rotation of shaft 111 causes gear 118 to also rotate about the longitudinal axis of the shaft 111. Shaft gear 118 engages the drive gear 107, causing it to rotate about axis 102 relative to the arm part 310. Carrier 104 is fast with the drive gear 107, and thus rotation of drive gear 107 causes carrier 104 to rotate about axis 102 relative to arm part 310. The rotation of carrier 104 about axis 102 drives the articulation of arm part 311 relative to arm part 310 about axis 102. Rotation of the carrier 104 about axis 102 causes articulations of universal joints 114 and 115 and the prismatic joint 116 to accommodate the rotation of shaft gear 113 relative to shaft gear 118 about axis 102.

To drive articulations about axis 103, motor 110 is operated to rotate the drive shaft 112. Rotation of the proximal end of drive shaft 112 is coupled to the rotation of the shaft gear 113 via the universal joints 114 and 115 (and the coupler 116). Shaft gear 113 engages the bevel gear 108. Thus rotation of shaft gear 113 drives rotation of gear 108 about axis 103 relative to the carrier 104. Bevel gear 108 is fast with the arm part 311, and thus rotation of gear 108 causes arm part 311 to be articulated with respect to arm part 310 about axis 103.

Rotation of drive shaft 111 whilst shaft 112 is kept stationary may cause parasitic motion of arm part 311 about axis 103. This is because the rotation of the carrier 104 about axis 102 may cause a rotation of the universal joints 114 and 115 which drives rotation of worm 113 and thus bevel 108. To prevent this parasitic motion, control system 10 may be arranged to operate the motor 109 to drive rotation of shaft 111 to cause the rotation of arm part 311 relative to arm part 310 about axis 102 whilst simultaneously operating the motor 110 to drive rotation of shaft 112 in such a way as to prevent parasitic rotation about axis 103. The control system 10 may be configured to operate in this manner when the robot arm is commanded to articulate about axis 102 without articulating about axis 103.

Control system 10 may also be configured to drive rotation of shaft 112 in such a way as to reduce irregularities in the rotation of universal joints 114 and 115. The Hooke's joints may experience irregular or inconsistent rotation when they are off-axis, i.e. when arm part 311 is in pitch relative to arm part 310. Thus when the arm part 311 is commanded to articulate relative to arm part 310 about axis 103 when arm part 311 is in pitch relative to arm part 310, the control system 10 may operate to drive the rotation of shaft 112 in such a way as to maintain a smooth or consistent rotation speed of the Hooke's joints 114 and 115. This may help to provide a smooth and/or consistent rotation about axis 103.

Various aspects of the mechanism shown in FIGS. 7 to 10 are advantageous in helping to make the mechanism particularly compact. For example:

It is convenient for bevel gear 107 to be of part-circular form: i.e. its teeth do not encompass a full circle. For example, gear 107 may encompass less than 270° or less than 180° or less than 90°. This allows at least part of the other bevel gear 108 to be located in such a way that it intersects a circle coincident with gear 107, about the axis of gear 107 and having the same radius as the outermost part of gear 107. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 102 is restricted.

It is convenient if the worms 118 and 113 are located on opposite sides of the bevel gear 107. In other words, bevel gear 107 may be interposed between the worms 113 and 118. This may help to provide a compact packaging arrangement. The gears 107 and/or 108 are conveniently provided as bevel gears since that permits them to be driven from worms located within the plan of their respective external radii. However, they could be externally toothed gears engaged on their outer surfaces by the worms attached to shafts 111, 112, or by externally toothed gears.

The bevel gears and the worm gears that mate with them can conveniently be of skew axis, e.g. Spiroid®, form. These allow for relatively high torque capacity in a relatively compact form.

Various changes can be made to the mechanisms described above. For example, and without limitation:
- The axes corresponding to axes 305, 306 need not intersect and need not be orthogonal. In general, the axes corresponding to axes 305 and 306 are two non-parallel rotation axes. They may be substantially perpendicular to each other in all configurations of the joints 301 and 302. Each axis may be substantially transverse to the longitudinal direction of the arm part 310 in at least one configuration of the joints 301 and 302. One such configuration is when arm part 311 is neither in pitch or yaw relative to arm part 310.
- The axes corresponding to axes 305 and 306 are non-parallel but need not be orthogonal to each other. Axis 305 is non-parallel to axis 304 but need not be orthogonal to it. Axis 306 is non-parallel to axis 307 but need not be orthogonal to it.
- The axes corresponding to axes 304 and 307 need not be parallel and collinear; they could be parallel but no collinear. For example, arm part 3b could be cranked relative to arm part 3c.
- The bevel gears or their outer toothed gear equivalents need not be driven by worms. They could be driven by other gears. They could for example be driven by pinions.
- Thus the drive gears may be bevel gears or other types of ring gear, such as externally toothed gears, i.e. gears with teeth extending in the radial direction. The shaft gears could be worms or other types of gears such as pinions, e.g. bevel gears.
- Either or both bevel gears could be part gears. More generally, either or both drive gears could be part gears.
- In the examples given above, the mechanisms form part of a wrist for a robot arm. The mechanisms could be used for other applications, for example for other parts of robot arms, for robot tools, and for non-robotic applications such as control heads for cameras.

As discussed above with reference to FIG. 1, each joint is provided with a torque sensor which senses the torque applied about the axis of that joint. Data from the torque sensors is provided to the control unit 10 for use in controlling the operation of the arm.

Figure 9:
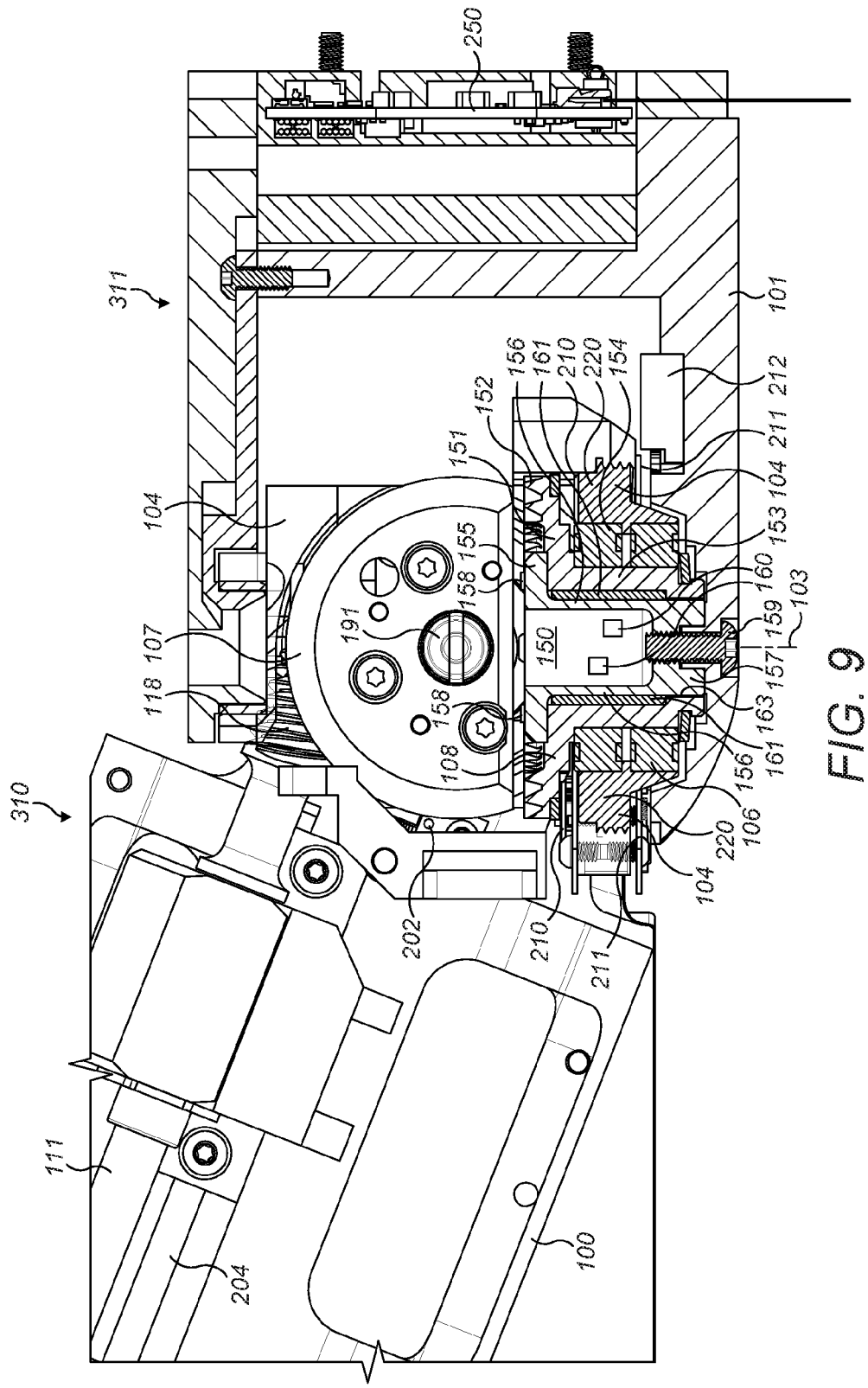
FIG. 9 shows the third wrist mechanism in section on a central longitudinal plane viewed from one side.

FIGS. 9 and 10 shows one of the torque sensors and its mounting arrangement in cross-section. Torque sensor 150 measures the torque applied about axis 103: that is from carrier 104 to distal arm frame 101. As described above, bevel gear 108 is fast with frame 101 and rotatable about axis 103 with respect to the carrier 104. Bevel gear 108 comprises a radially extending gear portion 151, from which its gear teeth 152 extend in an axial direction, and an axially extending neck 153. The neck, the radially extending gear portion and the teeth are integral with each other. The interior and exterior walls of the neck 153 are of circularly cylindrical profile. A pair of roller or ball bearing races 106, 154 fit snugly around the exterior of the neck. The bearings sit in cups in the carrier 104 and hold the neck 153 in position relative to the carrier whilst permitting rotation of the bevel gear 108 relative to the carrier about axis 103.

The torque sensor 150 has a radially extending top flange 155, an axially elongate torsion tube 156 which extends from the top flange, and an internally threaded base 157 at the end of the torsion tube opposite the flange. The top flange 155 abuts the gear portion 151 of the bevel gear 108. The top flange is held fast with the gear portion by bolts 158. The torsion tube 156 extends inside the neck 153 of the bevel gear 108. The exterior wall of the torsion tube is of circularly cylindrical profile. The exterior of the base 157 is configured with a splined structure which makes positive engagement with a corresponding structure in the frame 101 so as to hold the two in fixed relationship about axis 103. A bolt 159 extends through the frame 101 and into the base 157 to clamp them together. Thus, it is the torque sensor 150 that attaches the bevel gear 108 to the arm frame 101, and the torque applied about axis 103 is applied through the torque sensor. The torsion tube has a hollow interior and a relatively thin wall to its torsion tube 150. When torque is applied through the torque sensor there is slight torsional distortion of the torsion tube. The deflection of the torsion tube is measured by strain gauges 160 fixed to the interior wall of the torsion tube. The strain gauges form an electrical output indicative of the torsion, which provides a representation of the torque about axis 103. The strain gauges could be of another form: for example optical interference strain gauges which provide an optical output.

In order to get the most accurate output from the torque sensor, torque transfer from the bevel gear 108 to the frame 101 in a way that bypasses the torsion tube 156 should be avoided. For that reason, it is preferred to reduce friction between the neck 153 of the bevel gear 108 and the base 157 of the torque sensor. One possibility is to provide a gap between the neck of the bevel gear and both the base of the torque sensor and the torsion tube. However, that could permit shear forces to be applied to the torsion tube in a direction transverse to axis 103, which would itself reduce the accuracy of the torque sensor by exposing the strain gauges 160 to other than torsional forces. Another option is to introduce a bearing race between the interior of the neck of bevel gear 108 and the exterior of the base 157 of the torque sensor. However, that would substantially increase the volume occupied by the mechanism. Instead, the arrangement shown in FIG. 8 has been shown to give good results. A sleeve or bushing 161 is provided around the torsion tube 156 and within the neck 153 of the bevel gear 108. The sleeve is sized so that it makes continuous contact with the interior wall of the neck 153 and with the exterior wall of the torsion tube 156, which is also of circularly cylindrical profile. The whole of the interior surface of the sleeve makes contact with the exterior of the torsion tube 156. The whole of the exterior surface of the sleeve makes contact with the interior surface of the neck 153. The sleeve is constructed so that it applies relatively little friction between the neck and the torsion tube: for instance the sleeve may be formed of or coated with a low-friction or self-lubricating material. The sleeve is formed of a substantially incompressible material so that it can prevent deformation of the torque sensor under shear forces transverse to the axis 103. For example, the sleeve may be formed of or coated with a plastics material such as nylon, polytetrafluoroethylene (PTFE), polyethylene (PE) or acetal (e.g. Delrin®), or of graphite or a metal impregnated with lubricant.

For easy assembly of the mechanism, and to hold the sleeve 161 in place, the interior wall of the neck 153 of the bevel gear 108 is stepped inwards at 162, near its end remote from the radially extending gear portion 151. When the sleeve 161 is located between the neck 153 and the torsion tube 156, and the head 155 of the torque sensor is bolted to the gear portion 151 the sleeve is held captive both radially (between the torsion tube and the neck) and axially (between the head 155 of the torque sensor and the step 162 of the interior surface of the neck 153 of the bevel gear). It is preferred that the internal radius of the neck 153 in the region 163 beyond the step 162 is such that the internal surface of the neck in that region is spaced from the torque sensor 150, preventing frictional torque transfer between the two.

Similar arrangements can be used for the torque sensor about the other axis 102 of the embodiment of FIGS. 7 to 10, and for the torque sensors of the embodiments of the other figures.

Hall effect sensors are used to sense the rotational position of the joints. Each position sensor comprises a ring of material arranged around one of the rotation axes. The ring has a series of regularly spaced alternating north and south magnetic poles. Adjacent to the ring is a sensor chip with a sensor array comprising multiple Hall effect devices which can detect the magnetic field and measure the position of the magnetic poles on the ring relative to the sensor array so as to provide a multi-bit output indicative of that relative position. The rings of magnetic poles are arranged such that each position of the respective joint within a 360° range is associated with a unique set of outputs from the pair of magnetic sensors. This may be achieved by providing different numbers of poles on each ring and making the numbers of poles the rings co-prime to each other. Hall effect position sensors employing this general principle are known for use in robotics and for other applications.

More specifically, associated with each joint is a pair of alternatingly magnetised rings, and associated sensors. Each ring is arranged concentrically about the axis of its respective joint. The rings are fast with an element on one side of the joint and the sensors are fast with an element on the other side of the joint, with the result that there is relative rotational motion of each ring and its respective sensor when there is rotation of the robot arm about the respective joint. Each individual sensor measures where between a pair of poles the associated ring is positioned relative to the sensor. It cannot be determined from the output of an individual sensor which of the pole pairs on the ring is above the sensor. Thus the individual sensors can only be used in a relative fashion and would require calibration at power up to know the absolute position of the joint. However by using a pair of rings designed so that the numbers of pole pairs in each ring has no common factors it is possible to combine the inter-pole pair measurement from both sensors and work out the absolute position of the joint without calibration.

The magnetic rings and sensors are shown in FIGS. 7 to 10. For the joint that provides rotation about axis 102 position is sensed by means of magnetic rings 200 and 201 and sensors 202 and 203. For the joint that provides rotation about axis 103 position is sensed by means of magnetic rings 210, 211, sensor 212 and a further sensor that is not shown. Magnetic ring 200 is fast with carrier 104 and mounted on one side of the carrier. Magnetic ring 201 is fast with carrier 104 and mounted on the other side of the carrier to magnetic ring 200. The magnetic rings 200, 201 are planar, and arranged perpendicular to and centred on axis 102. Sensors 202 and 203 are fast with the frame 100 of the arm part 310. Sensor 202 is mounted so as to be adjacent to a side of ring 200. Sensor 203 is mounted so as to be adjacent to a side of ring 201. Cables 204, 205 carry the signals from the sensors 202, 203. Magnetic ring 210 is fast with carrier 104 and mounted on one side of a flange 220 of the carrier. Magnetic ring 211 is fast with carrier 104 and mounted on the other side of the flange 220 to magnetic ring 200. The magnetic rings 210, 211 are planar, and arranged perpendicular to and centred on axis 103. Sensor 212 and the other sensor for rotation about axis 103 are fast with the frame 101 of the arm part 311. Sensor 212 is mounted so as to be adjacent to a side of ring 210. The other sensor is mounted so as to be adjacent to a side of ring 211.

Thus, in the arrangement of FIGS. 7 to 10, rotation about each of the axes 102, 103 is sensed by means of two multipole magnetic rings, each with a respective associated sensor. Each sensor generates a multi-bit signal representing the relative position of the nearest poles on the respective ring to the sensor. By arranging for the numbers of poles on the two rings to be co-prime the outputs of the sensors are in combination indicative of the configuration of the joint within a 360° range. This permits the rotation position of the joint to be detected within that range. Furthermore, in the arrangement of FIGS. 7 to 10 the two rings associated with each joint (i.e. rings 200, 201 on the one hand and rings 210, 211 on the other hand) are located so as to be substantially offset from each other along the axis of the respective joint. Ring 200 is located near the bearing 190 on one side of the body of carrier 104 whereas ring 201 is located near bearing 105 on the opposite side of the carrier 104. Ring 210 is located on one side of the flange 220 whereas ring 211 is located on the other side of the flange 220. Each ring is made of a sheet of material which is flat in a plane perpendicular to the axis about which the ring is disposed. The magnetic rings of each pair (i.e. rings 200, 201 on the one hand and rings 210, 211 on the other hand) are spaced from each other in the direction along their respective axes by a distance greater than 5 and more preferably greater than 10 or greater than 20 times the thickness of the rings of the pair. Conveniently, the rings of a pair can be on opposite sides of the respective joint, as with rings 200, 201. Conveniently the carrier 104 to which the both rings of a pair are attached extends radially outwardly so as to lie at a radial location that is between the rings when viewed in a plane containing the respective rotation axis. Thus, for example, flange 220 lies radially between rings 210 and 211. Conveniently the respective joint can be supported or defined by two bearings, one on either side of the joint along the respective axis, and at extreme locations on the joint, and the or each ring for that joint can overlap a respective one of the bearings in a plane perpendicular to the axis. Conveniently the sensors for the rings can be mounted on an arm part that is articulated by the joint. The sensors can be mounted on opposite sides of the arm part.

By spacing the rings apart the packaging of the joint and/or of the arm part where the associated sensors are mounted can be greatly improved. Spacing the rings apart allows for more opportunities to locate the rings at a convenient location, and allows the sensors to be spaced apart, which can itself provide packaging advantages. It is preferred that the joint is sufficiently stiff in comparison to the number of magnetic poles on the rings that torsion of the joint under load will not adversely affect measurement. For example it is preferred that the joint is sufficiently stiff that under its maximum rated operating load the elements of the joint cannot twist so much that it can cause a change in the order of magnetic transitions at the sensors, even though they are spaced apart. That permits direction to be detected, in addition to motion, for all load conditions.

Arm part 311 is distal of arm part 310. Arm part 310 is proximal of the joint about axes 102 and 103 shown in FIGS. 7 to 10. As discussed with reference to FIG. 1, data from the torque sensors and the position sensors to be fed back to the control unit 10. It is desirable for that data to be passed by wired connections that run through the arm itself.

Each arm part comprises a circuit board. FIGS. 7 to 10 show a circuit board 250 carried by arm part 311. Each circuit board includes a data encoder/decoder (e.g. integrated circuit 251). The encoder/decoder converts signals between formats used locally to the respective arm part and a format used for data transmission along the arm. For example: (a) locally to the arm part the position sensors may return position readings as they are passed by magnetic pole transitions, the torque sensor may return an analogue or digital signal indicative of the currently sensed torque and the drive motors may require a pulse width modulated drive signal; whereas (b) for data transmission along the arm a generic data transmission protocol, which may be a packet data protocol such as Ethernet, can be used. Thus the encoders/decoders can receive data packets conveyed along the arm from the control unit 10 and interpret their data to form control signals for any local motor, and can receive locally sensed data and convert it into packetised form for transmission to the control unit. The circuit boards along the arm can be chained together by communication cables, so that communications from a relatively distal board go via the more proximal boards.

In general it is desirable not to feed data from one component of the arm to a more distal component of the arm. Doing so would involve cables running unnecessarily distally in the arm, increasing distally distributed weight; and since the circuit boards are chained together once data has been sent to a relatively distal board the next most proximal board will handle the data anyway in order to forward it.

The compound joint about axes 102, 103 has rotary position sensors 202, 203 (for rotation about axis 102) and 212 (for rotation about axis 103). Sensors 202, 203 are mounted on the frame 100 of the arm part 310 that is proximal of the joint whose motion is measured by the sensor. Data from position sensors 202, 203 is fed along cables 204, 205 which lead along arm part 310 proximally of the sensors. Sensor 202 is mounted on the frame 101 of the arm part 311. Data from position sensor 202 is fed along a cable to circuit board 250 on the same arm part. In each case the data is not passed to a more distal element of the arm than the one where the data was collected.

The compound joint about axes 102, 103 has torque sensors 150 (for rotation about axis 103) and 191 (for rotation about axis 102). Data sensed by torque sensors 150, 191 is carried in native form to circuit board 250 by flexible cables. At circuit board 250 the encoder/decoder 251 encodes the sensed data, e.g. to Ethernet packets, and transmits it to the control unit 10. Thus, rather than being fed to the circuit board of the more proximal arm part 310 for encoding, the data from the torque sensors is passed to the circuit board of the more distal arm part for encoding, and then from that circuit board it is passed by cables in a distal direction along the arm.

Figure 11:
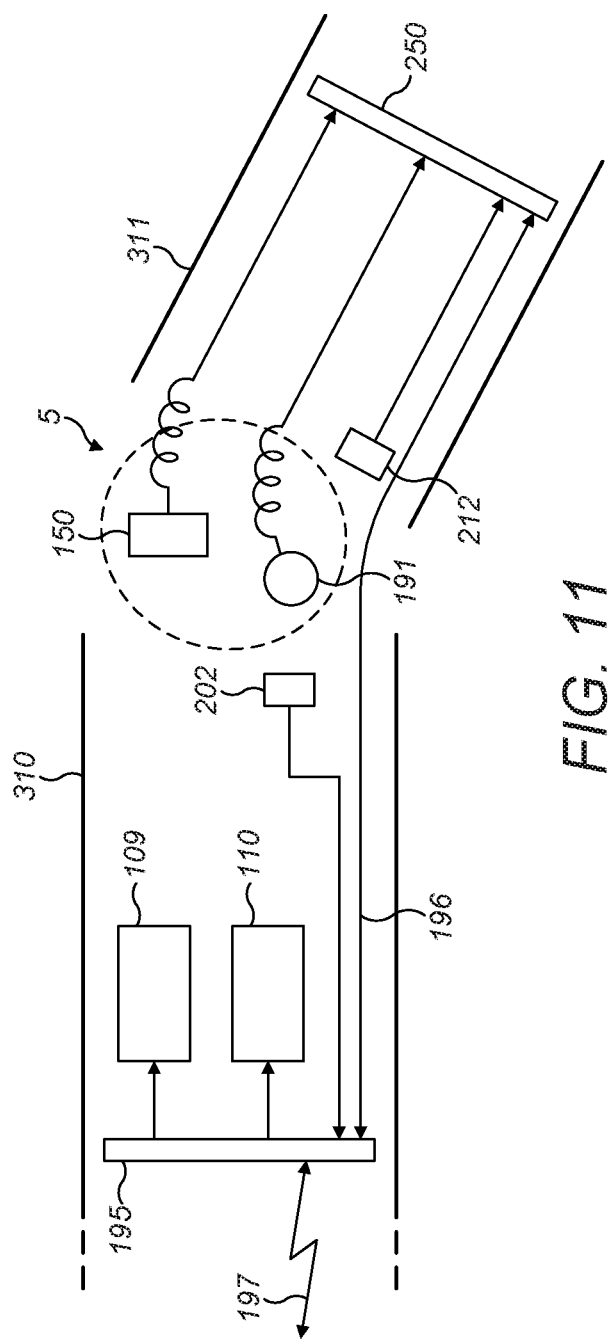
FIG. 11 illustrates communication paths in a robot arm.

This arrangement is illustrated in FIG. 11. Arm part 310 comprises circuit board 195 which receives data from position sensor 202 and provides command data to motors 109, 110. Arm part 311 comprises circuit board 250 which receives data from position sensor 212 and torque sensors 150, 191. Circuit board 250 encodes that sensed data and passes it over a data bus 196 to circuit board 195, which forwards it on towards control unit 10 via a link 197. Position sensor 202 is connected directly by a cable to circuit board 195. Position sensor 212 and torque sensors 150, 191 are connected directly by cables to circuit board 195.

Figure 12:
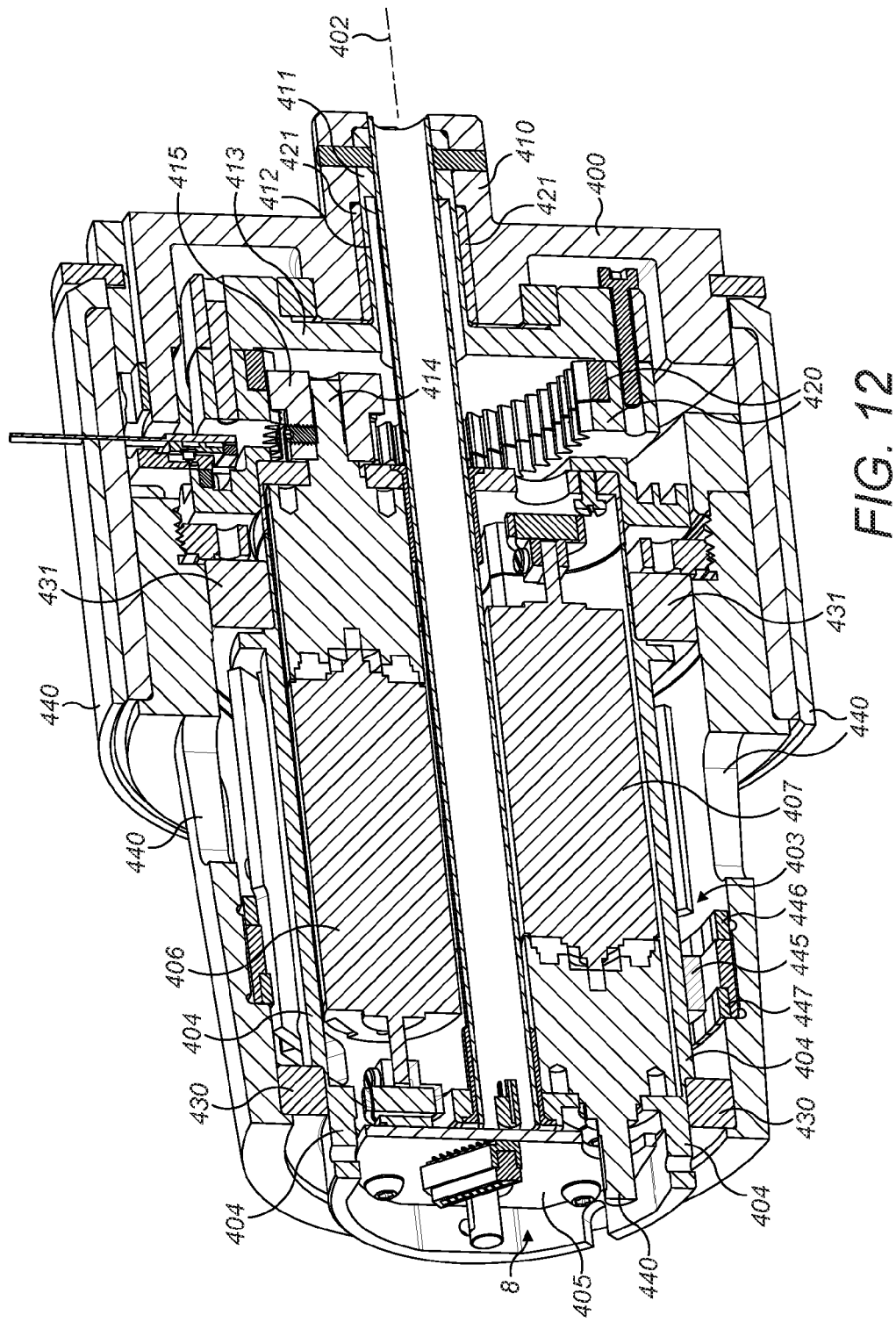
FIG. 12 shows a terminal module for a robot arm in longitudinal cross-section.

As illustrated in FIG. 2, arm part 4c is borne by arm part 311 and can be rotated relative to arm part 4c about axis 307. FIG. 12 shows a cross-section through a module that comprises arm part 4c. The module has a base 400 and a side-wall 440 which is fast with the base. Base 400 attaches to the end face 401 of the distal end of arm part 311. (See FIG. 7). Arm part 4c is indicated generally at 403. Arm part 4c is rotatable relative to the base about an axis 402 corresponding to axis 307 of FIG. 2. To that end, arm part 4c is mounted to the side-wall 440 by bearings 430, 431 which define a revolute joint between side wall 440 and arm part 4c about axis 402.

Arm part 4c has a housing 404 which houses its internal components. Those components include a circuit board 405 and motors 406, 407. Motors 406, 407 are fixed to the housing 404 so they cannot rotate relative to it. The housing 404 is free to rotate relative to the base 400 by means of the bearings 430, 431. A channel 408 runs through the interior of the module to accommodate a communication cable (not shown) passing from circuit board 250 to circuit board 405. The communication cable carries signals which, when decoded by an encoder/decoder of circuit board 405, cause it to issue control signals to control the operation of motors 406, 407.

Motor 406 drives rotation of arm part 4c relative to arm part 311. Thus, motor 406 drives rotation of housing 404 relative to base 400. Base 400 has a central boss 410. A torque sensor generally of the type discussed in relation to FIGS. 9 and 10 is attached to the boss 410. The torque sensor has an integral member comprising a base 411, a torsion tube 412 and a radially extending head 413. The base 411 of the torque sensor is fast with the boss 410 of the base 400. As with the torque sensor of FIGS. 9 and 10, a sleeve 421 extends around the torsion tube of the torque sensor to protect it from shear forces and to reduce friction between it and the surrounding component, which is the base 400.

An internally toothed gear 420 is fast with the head 413 of the torque sensor. Motor 406 drives a shaft 414 which carries a pinion gear 415. Pinion gear 415 engages the internal gear 420. Thus, when the motor 406 is operated it drives the pinion gear 415 to rotate and this causes the arm part 4c, of which the motor 406 is part, to rotate about axis 402. The resulting torque about axis 402 is transmitted to the base 400 through the torsion tube 412 of the torque sensor, allowing that torque to be measured by strain gauges attached to the torsion tube.

The interface 8 for attachment to an instrument is shown in FIG. 12. The shaft 440 of motor 407 is exposed at the interface for providing drive to an instrument.

Torque data from the torque sensor 411, 412, 413 is passed to circuit board 250 on arm part 311 for encoding. The rotational position of arm part 4c can be sensed by a sensor 445 carried by arm part 4c and which detects transitions between magnetic poles on rings 446, 447 mounted on the interior of housing 404. Data from sensor 445 is passed to circuit board 405 of arm part 4c for encoding.

The motors that drive rotation about joints 102 and 103 are mounted proximally of those joints, in arm part 310. As discussed above, this improves weight distribution by avoiding weight being placed nearer to the distal end of the arm. In contrast, the motor that drives rotation of arm part 4c is mounted in arm part 4c rather than in arm part 311. Although this might be seen as disadvantageous due to it requiring motor 406 to be mounted more distally, it has been found that this allows for arm part 311 to be especially compact. Motor 406 can be packaged in arm part 4c in parallel with the motor(s) (e.g. 407) which provide drive to the instrument: i.e. so that the motors intersect a common plane perpendicular to the axis 402. That means that incorporation of motor 406 in arm part 4c need not make arm part 4c substantially longer.

Instead of toothed gears, the drive of the joints could be by frictional means.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A robot arm comprising a joint mechanism for articulating one limb of the arm relative to another limb of the arm about two non-parallel rotation axes, the mechanism comprising:
    an intermediate carrier attached to a first one of the limbs by a first revolute joint having a first rotation axis and to a second one of the limbs by a second revolute joint having a second rotation axis;
    a first drive gear disposed about the first rotation axis, the first drive gear being fast with the carrier;
    a second drive gear disposed about the second rotation axis, the second drive gear being fast with the second one of the limbs;
    a first drive shaft for driving the first drive gear to rotate about the first rotation axis, the first drive shaft extending along the first one of the limbs and having a first shaft gear thereon, the first shaft gear being arranged to engage the first drive gear;
    a second drive shaft for driving the second drive gear to rotate about the second rotation axis, the second drive shaft extending along the first one of the limbs and having a second shaft gear thereon, the second shaft gear being arranged to engage the second drive gear;
    the second drive shaft comprising a prismatic joint whereby the length of the shaft can vary in response to motion of the carrier about the first axis.

2. A robot arm as claimed in claim 1, wherein the prismatic joint is a sliding splined coupling.

3. A robot arm as claimed in claim 1, wherein the second dive shaft comprises a first flexible joint on one side of the prismatic joint and a second flexible joint on the other side of the prismatic joint.

4. A robot arm as claimed in claim 3, wherein the second drive shaft is connected by a revolute joint to the carrier on the opposite side of the second flexible joint to the prismatic joint.

5. A robot arm as claimed in claim 1, wherein one or both of the first and second shaft gears is/are worm gears.

6. A robot arm as claimed in claim 1, wherein one or both of the first drive gears is/are bevel gear(s).

7. A robot arm as claimed in claim 6, wherein one or both of the first drive gears is/are skew axis gear(s).

8. A robot arm as claimed in claim 1, wherein the first drive gear is a part-circular gear.

9. A robot arm as claimed in claim 8, wherein at least part of the second drive gear intersects a circle about the first axis that is coincident with the radially outermost part of the first drive gear.

10. A robot arm as claimed in claim 5, wherein the first and second axes are orthogonal.

11. A robot arm as claimed in claim 5, wherein the first and second axes intersect each other.

12. A robot arm as claimed in any preceding claim, further comprising a control unit arranged to respond to command signals commanding rotation of the robot arm by driving the first and second drive shafts to rotate, the control unit being configured to, when the robot arm is commanded to articulate about the first axis without articulating about the second axis, drive the first shaft to rotate to cause articulation about the first axis and also drive the second shaft to rotate in such a way as to negate parasitic articulation about the second axis.

13. A robot arm as claimed in any preceding claim, further comprising a control unit arranged to respond to command signals commanding rotation of the robot arm by driving the first and second drive shafts to rotate, the control unit being configured to, when the robot arm is commanded to articulate about the second rotation axis when the second one of the limbs is articulated with respect to the first one of the limbs about the first rotation axis, drive the second drive shaft to rotate to cause articulation about the second axis in such a way as to provide smooth rotation about the second axis.

* * * * *